(12) United States Patent
Parfenov et al.

(10) Patent No.: US 8,057,400 B2
(45) Date of Patent: Nov. 15, 2011

(54) SYSTEM AND METHOD OF MEASURING CHANGES IN ARTERIAL VOLUME OF A LIMB SEGMENT

(75) Inventors: Alexander S. Parfenov, Moscow (RU); Maria A. Parfenova, Mountain View, CA (US); Nikolay V. Konstantinov, Moscow (RU)

(73) Assignee: Angiologix, Inc., Ann Arbor, MI (US)

( * ) Notice: Subject to any disclaimer, the term of this patent is extended or adjusted under 35 U.S.C. 154(b) by 106 days.

(21) Appl. No.: 12/483,930

(22) Filed: Jun. 12, 2009

(65) Prior Publication Data
US 2010/0292592 A1 Nov. 18, 2010

Related U.S. Application Data

(60) Provisional application No. 61/177,341, filed on May 12, 2009.

(51) Int. Cl.
*A61B 5/02* (2006.01)
(52) U.S. Cl. .......... 600/507; 600/500
(58) Field of Classification Search .......... 600/507, 600/500–503, 504
See application file for complete search history.

(56) References Cited

U.S. PATENT DOCUMENTS

| | | |
|---|---|---|
| 3,807,389 A | 4/1974 | Miller |
| 3,903,872 A | 9/1975 | Link |
| 3,980,075 A | 9/1976 | Heule |
| 4,009,709 A | 3/1977 | Link |
| 4,074,711 A | 2/1978 | Link |
| 4,195,643 A | 4/1980 | Pratt |
| 4,432,374 A | 2/1984 | Osanai |
| 4,562,843 A | 1/1986 | Djordjevich |
| 4,566,463 A | 1/1986 | Taniguchi |
| 4,646,754 A | 3/1987 | Seale |
| 4,669,485 A | 6/1987 | Russell |
| 4,677,983 A | 7/1987 | Yamaguchi |
| 4,718,426 A | 1/1988 | Russell |
| 4,718,427 A | 1/1988 | Russell |
| 4,718,428 A | 1/1988 | Russell |
| 4,771,792 A | 9/1988 | Seale |
| 4,846,189 A | 7/1989 | Sun |
| 4,850,371 A | 7/1989 | Broadhurst |

(Continued)

FOREIGN PATENT DOCUMENTS

DE 102004016376 4/2004
(Continued)

OTHER PUBLICATIONS

PCT/US2010/033907 International Search Report and Written Opinion Jul. 6, 2010.
(Continued)

*Primary Examiner* — Patricia Mallari
*Assistant Examiner* — Christian Jang
(74) *Attorney, Agent, or Firm* — Baker & Hostetler LLP

(57) ABSTRACT

A medical diagnostic device performs diagnostics for assessing the ability of the arteries to respond to an increase in blood flow. The medical diagnostic device determines relative changes in arterial volume of the limb segment during a time period after a stimulus relative to the arterial volume of the limb segment during a baseline period using the amplitudes or other portions of the component pulse waves (such as early systolic components) of volume pulse waves during the baseline period and after the stimulus.

49 Claims, 15 Drawing Sheets

U.S. PATENT DOCUMENTS

| | | | |
|---|---|---|---|
| 4,880,013 A | 11/1989 | Chio | |
| 4,966,141 A | 10/1990 | Bacaner | |
| 4,979,110 A | 12/1990 | Albrecht | |
| 4,986,277 A | 1/1991 | Sackner | |
| 4,993,422 A | 2/1991 | Hon | |
| 5,025,792 A | 6/1991 | Hon | |
| 5,040,540 A | 8/1991 | Sackner | |
| 5,043,576 A | 8/1991 | Broadhurst | |
| 5,048,533 A | 9/1991 | Muz | |
| 5,054,494 A | 10/1991 | Lazzaro | |
| 5,099,852 A | 3/1992 | Meister | |
| 5,119,824 A | 6/1992 | Niwa | |
| 5,127,408 A | 7/1992 | Parsons | |
| 5,140,990 A | 8/1992 | Jones | |
| 5,152,297 A | 10/1992 | Meister | |
| 5,161,531 A | 11/1992 | Parsons | |
| 5,162,991 A | 11/1992 | Chio | |
| 5,241,963 A | 9/1993 | Shankar | |
| 5,241,964 A | 9/1993 | McQuilkin | |
| 5,269,310 A | 12/1993 | Jones | |
| 5,271,399 A | 12/1993 | Listerud | |
| 5,297,556 A | 3/1994 | Shankar | |
| 5,303,711 A | 4/1994 | Sciarra | |
| 5,343,867 A | 9/1994 | Shankar | |
| 5,379,774 A | 1/1995 | Nishimura | |
| 5,423,322 A | 6/1995 | Clark | |
| 5,447,163 A | 9/1995 | Apple | |
| 5,511,546 A | 4/1996 | Hon | |
| 5,533,511 A | 7/1996 | Kaspari | |
| 5,685,989 A | 11/1997 | Krivitski | |
| 5,758,652 A | 6/1998 | Nikolic | |
| 5,810,734 A | 9/1998 | Caro | |
| 5,830,131 A | 11/1998 | Caro | |
| 5,833,602 A | 11/1998 | Osemwota | |
| 5,876,347 A | 3/1999 | Chesney | |
| 5,906,581 A | 5/1999 | Tsuda | |
| 5,935,066 A | 8/1999 | Harris | |
| 5,980,464 A | 11/1999 | Tsuda | |
| 6,010,457 A | 1/2000 | O'Rourke | |
| 6,015,393 A | 1/2000 | Hovland | |
| 6,027,452 A | 2/2000 | Flaherty | |
| 6,045,509 A | 4/2000 | Caro | |
| 6,048,318 A | 4/2000 | Chesney | |
| 6,120,459 A | 9/2000 | Nitzan | |
| 6,152,881 A | 11/2000 | Raines | |
| 6,162,181 A | 12/2000 | Hynson | |
| 6,171,242 B1 | 1/2001 | Amano | |
| 6,210,591 B1 | 4/2001 | Krivitski | |
| 6,241,680 B1 | 6/2001 | Miwa | |
| 6,290,651 B1 | 9/2001 | Chesney | |
| 6,309,359 B1 | 10/2001 | Whitt | |
| 6,319,205 B1 | 11/2001 | Goor | |
| 6,322,515 B1 | 11/2001 | Goor | |
| 6,331,159 B1 | 12/2001 | Amano | |
| 6,331,161 B1 | 12/2001 | Chesney | |
| 6,338,719 B1 | 1/2002 | Drzewiecki | |
| 6,440,080 B1 | 8/2002 | Booth | |
| 6,445,945 B1 | 9/2002 | Arsenault | |
| 6,461,305 B1 | 10/2002 | Schnall | |
| 6,482,163 B2 | 11/2002 | Oka | |
| 6,491,647 B1 | 12/2002 | Bridger | |
| 6,517,495 B1 | 2/2003 | Hersh | |
| 6,554,774 B1 | 4/2003 | Miele | |
| 6,585,659 B1 | 7/2003 | Chesney | |
| 6,592,528 B2 | 7/2003 | Amano | |
| 6,616,613 B1 | 9/2003 | Goodman | |
| 6,623,431 B1 | 9/2003 | Sakuma | |
| 6,623,434 B2 | 9/2003 | Chesney | |
| 6,626,840 B2 | 9/2003 | Drzewiecki | |
| 6,629,343 B1 | 10/2003 | Chesney | |
| 6,632,181 B2 | 10/2003 | Flaherty | |
| 6,654,628 B1 | 11/2003 | Silber | |
| 6,662,130 B1 | 12/2003 | Peel | |
| 6,719,704 B2 | 4/2004 | Narimatsu | |
| 6,733,461 B2 | 5/2004 | Bratteli | |
| 6,746,407 B2 | 6/2004 | Steuer | |
| 6,749,567 B2 | 6/2004 | Davis | |
| 6,757,554 B2 | 6/2004 | Rubinstein | |
| 6,804,543 B2 | 10/2004 | Miller | |
| 6,868,739 B1 | 3/2005 | Krivitski | |
| 6,884,221 B2 | 4/2005 | Narimatsu | |
| 6,896,660 B2 | 5/2005 | Jelliffe | |
| 6,905,470 B2 | 6/2005 | Lee | |
| 6,908,436 B2 | 6/2005 | Chowienczyk | |
| 6,915,154 B1 | 7/2005 | Docherty | |
| 6,916,289 B2 | 7/2005 | Schnall | |
| 6,937,882 B2 | 8/2005 | Steuer | |
| 6,939,304 B2 | 9/2005 | Schnall | |
| 6,939,305 B2 | 9/2005 | Flaherty | |
| 6,987,993 B2 | 1/2006 | Steuer | |
| 6,994,675 B2 | 2/2006 | Sharrock | |
| 7,022,084 B2 | 4/2006 | Ogura | |
| 7,024,234 B2 | 4/2006 | Margulies | |
| 7,041,060 B2 | 5/2006 | Flaherty | |
| 7,048,691 B2 | 5/2006 | Miele | |
| 7,056,291 B2 | 6/2006 | Yokozeki et al. | |
| 7,070,569 B2 | 7/2006 | Heinonen | |
| 7,074,183 B2 | 7/2006 | Castellanos | |
| 7,077,809 B2 | 7/2006 | Wu | |
| 7,121,150 B2 | 10/2006 | Krivitski | |
| 7,131,949 B2 | 11/2006 | Hayano | |
| 7,204,798 B2 | 4/2007 | Zdeblick | |
| 7,214,192 B2 | 5/2007 | Poliac | |
| 7,244,225 B2 | 7/2007 | Loeb | |
| 7,250,031 B2 | 7/2007 | Hayano | |
| 7,264,594 B2 | 9/2007 | Shimazu | |
| 7,291,112 B2 | 11/2007 | Martin | |
| 7,297,280 B2 | 11/2007 | Krivitski | |
| 7,318,804 B2 | 1/2008 | Weitzel | |
| 7,374,541 B2 | 5/2008 | Amitzur et al. | |
| 2001/0025151 A1 | 9/2001 | Kimball | |
| 2002/0013533 A1 | 1/2002 | Oka | |
| 2002/0062086 A1 | 5/2002 | Miele | |
| 2002/0065471 A1 | 5/2002 | Amano | |
| 2002/0072681 A1 | 6/2002 | Schnall | |
| 2002/0111554 A1 | 8/2002 | Drzewiecki | |
| 2002/0183599 A1 | 12/2002 | Castellanos | |
| 2003/0004423 A1 | 1/2003 | Lavie | |
| 2003/0032885 A1 | 2/2003 | Rubinstein | |
| 2003/0036685 A1 | 2/2003 | Goodman | |
| 2003/0040675 A1 | 2/2003 | Sharrock | |
| 2003/0060690 A1 | 3/2003 | Jelliffe | |
| 2003/0065270 A1 | 4/2003 | Raines | |
| 2003/0191395 A1 | 10/2003 | Bowman | |
| 2003/0212336 A1 | 11/2003 | Lee | |
| 2003/0216652 A1 | 11/2003 | Narimatsu | |
| 2003/0229288 A1 | 12/2003 | Chowienczyk | |
| 2003/0236464 A1 | 12/2003 | Narimatsu | |
| 2004/0092832 A1* | 5/2004 | Schnall et al. | 600/490 |
| 2004/0116787 A1 | 6/2004 | Schnall | |
| 2004/0127800 A1 | 7/2004 | Kimball | |
| 2004/0167413 A1 | 8/2004 | Bratteli | |
| 2004/0210145 A1* | 10/2004 | Satoh et al. | 600/500 |
| 2004/0215093 A1 | 10/2004 | Rubenstein | |
| 2004/0230125 A1 | 11/2004 | Amano | |
| 2004/0254483 A1 | 12/2004 | Zdeblick | |
| 2004/0254485 A1 | 12/2004 | Wu | |
| 2004/0267141 A1 | 12/2004 | Amano | |
| 2005/0004476 A1 | 1/2005 | Payvar | |
| 2005/0020891 A1 | 1/2005 | Rubinstein | |
| 2005/0020928 A1 | 1/2005 | Arsenault | |
| 2005/0038346 A1 | 2/2005 | Miele | |
| 2005/0043608 A1 | 2/2005 | Haj-Yousef | |
| 2005/0070805 A1 | 3/2005 | Dafni | |
| 2005/0075531 A1 | 4/2005 | Loeb | |
| 2005/0085712 A1* | 4/2005 | Rapoport | 600/413 |
| 2005/0107710 A1 | 5/2005 | Nakayama | |
| 2005/0113652 A1 | 5/2005 | Stark | |
| 2005/0143633 A1 | 6/2005 | Jelliffe | |
| 2005/0171443 A1 | 8/2005 | Gorenberg | |
| 2005/0182434 A1 | 8/2005 | Docherty | |
| 2005/0228303 A1 | 10/2005 | Hayano | |
| 2005/0267381 A1 | 12/2005 | Benditt | |
| 2006/0009700 A1 | 1/2006 | Brumfield | |
| 2006/0015032 A1 | 1/2006 | Gordon | |
| 2006/0052713 A1 | 3/2006 | Poliac | |
| 2006/0064024 A1 | 3/2006 | Schnall | |

| | | | | | | |
|---|---|---|---|---|---|---|
| 2006/0079791 | A1 | 4/2006 | Letremy | JP | 20217796 | 2/1999 |
| 2006/0122489 | A1 | 6/2006 | Kato | JP | 24129979 | 10/2002 |
| 2006/0149152 | A1 | 7/2006 | Amitzur | JP | 26102252 | 10/2004 |
| 2006/0178585 | A1 | 8/2006 | Sharrock | JP | 26115979 | 10/2004 |
| 2006/0206030 | A1 | 9/2006 | Flaherty | JP | 26181261 | 12/2004 |
| 2006/0206032 | A1 | 9/2006 | Miele | RU | 2265391 | 1/2004 |
| 2006/0217614 | A1 | 9/2006 | Takala | WO | 8604801 | 8/1986 |
| 2006/0217615 | A1 | 9/2006 | Huiku | WO | 9002512 | 9/1989 |
| 2006/0229488 | A1 | 10/2006 | Ayre | WO | 8909017 | 10/1989 |
| 2006/0229506 | A1 | 10/2006 | Castellanos | WO | 9001895 | 3/1990 |
| 2006/0229519 | A1 | 10/2006 | Fujiwara | WO | 9207508 | 5/1992 |
| 2006/0241459 | A1 | 10/2006 | Tai | WO | 9222239 | 12/1992 |
| 2006/0247538 | A1 | 11/2006 | Davis | WO | 9305704 | 4/1993 |
| 2006/0258946 | A1 | 11/2006 | Hayano | WO | 9518564 | 7/1995 |
| 2006/0264755 | A1 | 11/2006 | Maltz | WO | 9709927 | 3/1997 |
| 2006/0287600 | A1 | 12/2006 | McEowen | WO | 9712545 | 4/1997 |
| 2007/0021673 | A1 | 1/2007 | Arbel | WO | 9714356 | 4/1997 |
| 2007/0021683 | A1 | 1/2007 | Benditt | WO | 9749328 | 12/1997 |
| 2007/0055163 | A1 | 3/2007 | Asada | WO | 9804182 | 2/1998 |
| 2007/0078351 | A1 | 4/2007 | Fujita | WO | 9842255 | 10/1998 |
| 2007/0106162 | A1 | 5/2007 | Illyes et al. | WO | 0032103 | 11/1998 |
| 2007/0118045 | A1 | 5/2007 | Naghavi | WO | 9934724 | 7/1999 |
| 2007/0161914 | A1 | 7/2007 | Zdeblick | WO | 9939634 | 8/1999 |
| 2007/0173727 | A1 | 7/2007 | Naghavi | WO | 9963884 | 12/1999 |
| 2007/0225606 | A1 | 9/2007 | Naghavi | WO | 0017615 | 3/2000 |
| 2007/0270720 | A1 | 11/2007 | Fry | WO | 0059372 | 3/2000 |
| 2008/0004511 | A1 | 1/2008 | Rubinstein | WO | 0122870 | 8/2000 |
| 2008/0015434 | A1 | 1/2008 | Rubinstein | WO | 0057776 | 10/2000 |
| 2008/0027298 | A1 | 1/2008 | Blanco | WO | 0074551 | 12/2000 |
| 2008/0027330 | A1 | 1/2008 | Naghavi | WO | 0074563 | 12/2000 |
| 2008/0033307 | A1 | 2/2008 | Baudoin | WO | 0164101 | 9/2001 |
| 2008/0039731 | A1 | 2/2008 | McCombie | WO | 0170303 | 9/2001 |
| 2008/0139949 | A1 | 6/2008 | Caldarone et al. | WO | 0195798 | 12/2001 |
| | | | | WO | 02005726 | 1/2002 |
| FOREIGN PATENT DOCUMENTS | | | | WO | 0294085 | 5/2002 |
| EP | | 197302 | 3/1986 | WO | 02034105 | 5/2002 |
| EP | | 244264 | 5/1987 | WO | 0200107 | 6/2002 |
| EP | | 347101 | 6/1989 | WO | 0299600 | 6/2002 |
| EP | | 716829 | 5/1990 | WO | 02080752 | 10/2002 |
| EP | | 443267 | 8/1991 | WO | 02089668 | 11/2002 |
| EP | | 557492 | 9/1992 | WO | 03086169 | 4/2003 |
| EP | | 262778 | 6/1993 | WO | 03051193 | 6/2003 |
| EP | | 365614 | 6/1995 | WO | 2004006748 | 1/2004 |
| EP | | 694283 | 7/1995 | WO | 2004066817 | 1/2004 |
| EP | | 818175 | 11/1996 | WO | 2004012595 | 2/2004 |
| EP | | 431066 | 4/1997 | WO | 2004021878 | 3/2004 |
| EP | | 997102 | 9/1999 | WO | 2004041079 | 5/2004 |
| EP | | 1143852 | 8/2000 | WO | 2004052196 | 6/2004 |
| EP | | 1849408 | 8/2000 | WO | 2005006975 | 1/2005 |
| EP | | 1852061 | 8/2000 | WO | 2005028029 | 3/2005 |
| EP | | 1852063 | 8/2000 | WO | 2005092178 | 3/2005 |
| EP | | 588982 | 3/2001 | WO | 2005030038 | 4/2005 |
| EP | | 1175864 | 4/2001 | WO | 2006034542 | 9/2005 |
| EP | | 855874 | 1/2002 | WO | 2005110051 | 11/2005 |
| EP | | 1362549 | 2/2003 | WO | 2006024871 | 3/2006 |
| EP | | 1360929 | 3/2003 | WO | 2006102511 | 3/2006 |
| EP | | 1374760 | 3/2003 | WO | 2007024777 | 3/2007 |
| EP | | 1584289 | 3/2005 | WO | 2007030810 | 3/2007 |
| EP | | 857034 | 6/2005 | WO | 2007136526 | 5/2007 |
| EP | | 1618840 | 6/2005 | WO | 2007147069 | 6/2007 |
| EP | | 1704818 | 3/2006 | | | |
| EP | | 955868 | 8/2006 | | | |
| EP | | 1743572 | 1/2007 | | | |
| EP | | 1769748 | 4/2007 | | | |
| JP | | 5305061 | 5/1992 | | | |
| JP | | 7124129 | 5/1994 | | | |
| JP | | 9173307 | 12/1995 | | | |

OTHER PUBLICATIONS

Tsui et al., Arterial Pulse waveform analysis by the probability distribution of amplitude, Physiological Measurement, vol. 28, No. 8. 2007.

* cited by examiner

SYSTEM AND METHOD OF MEASURING CHANGES IN ARTERIAL VOLUME OF A LIMB SEGMENT

CROSS REFERENCE TO RELATED APPLICATION

This application claims a benefit of, and priority under 35 USC §119(e) to, U.S. Provisional Patent Application No. 61/177,341, filed May 12, 2009, and titled "System And Method Of Measuring Changes In Arterial Volume Of A Limb Segment", which is incorporated herein by reference in its entirety.

FIELD

The present invention relates generally to assessing changes in the arterial volume of a limb segment.

BACKGROUND

Cardiovascular disease is a leading cause of morbidity and mortality. It has been shown that the early stages of cardiovascular disease can be diagnosed by assessing the ability of the arteries to dilate in response to an increase in blood flow. The degree of arterial dilation in response to an increased blood flow correlates with the severity of cardiovascular disease.

Endothelial cells constitute the innermost lining of blood vessels and produce nitric oxide, which is the predominant vasodilator in the arterial system. An increase in blood flow results in increased shear stress at the surface of endothelial cells and initiates a signaling pathway that results in phosphorylation and activation of nitric oxide synthase, and increased production of nitric oxide. In addition to acting as a potent vasodilator, endothelium-derived nitric oxide inhibits many of the initiating steps in the pathogenesis of atherosclerotic cardiovascular disease, including low-density lipoprotein uptake, white cell adhesion to the vessel wall, vascular smooth muscle proliferation, and platelet adhesion and aggregation.

Brachial artery flow-mediated dilation serves as a measure of the bioavailability of endothelium-derived nitric oxide in patients, and it has been used extensively in large clinical studies to non-invasively detect endothelial dysfunction of the conduit artery.

Several invasive and non-invasive techniques have been developed to evaluate endothelial function. Invasive techniques, which involve intra-coronary or intra-brachial infusions of vasoactive agents, are considered to be the most accurate for the detection of endothelial dysfunction. Due to their highly invasive nature, the use of such techniques is limited and has led to the development of several non-invasive techniques. The ultrasound imaging of the brachial artery is the most commonly employed non-invasive technique for the assessment of the vasomotor response. See, for example, Mary C. Corretti et al. *J. Am. Coll. Cardiol.* 2002; 39:257-265, which is incorporated herein by reference in its entirety. It utilizes continuous electrocardiogram (EKG) gated two-dimensional ultrasound imaging on the brachial artery before and after induction of arterial dilation by five-minute cuff occlusion of the arm. The ultrasound imaging technique is mostly used to assess (1) the changes in the diameter of the brachial artery induced by administration of vasoactive drugs; and (2) flow-mediated dilation, which follows an occlusion of the brachial artery via inflating a cuff around the limb. Once the cuff is released, the blood flow causes shear stress on the endothelium, which, in turn, produces vasoactive substances that induce arterial dilation. The increase in the diameter of the brachial artery in healthy people is higher than that in patients with endothelial dysfunction. However, even in healthy people, the magnitude of the arterial dilation is not sufficient to be reliably determined by the ultrasound imaging technique. A trained and experienced operator is essential in obtaining meaningful data with the ultrasound imaging technique. This difficulty limits the testing of arterial dilation with the ultrasound imaging technique to specialized vascular laboratories.

Most of the existing techniques do not quantify the amount of stimulus delivered to the endothelium nor do they account for other sources of nitric oxide such as the nitric oxide transported and released by the blood cells in response to hypoxemia induced by the temporary occlusion of the brachial artery. It has been shown that these factors can significantly affect the amount of flow-mediated dilation and, therefore, inject additional variability into the test results obtained with equipment that does not account for such factors.

U.S. Pat. No. 6,152,881 (to Rains et. al.), which is incorporated herein by reference in its entirety, describes a method of assessing endothelial dysfunction by determining changes in arterial volume based on measured blood pressure using a pressure cuff. The pressure cuff is held near diastolic pressure for about ten minutes after an artery occlusion until the artery returns to its normal state. The measured pressure during this time is used to determine the endothelial function of the patient. The extended period of applying cuff pressure to the limb affects circulation, which in turn impacts the measurements.

U.S. Pat. No. 7,390,303 (to Dafni), which is incorporated herein by reference in its entirety, describes a method of assessing arterial dilation and endothelial function, in which the relative changes in the cross sectional area of a limb artery are assessed using a bio-impedance technique to monitor cross-sectional area of a conduit artery. Measurements of bio-impedance are difficult to perform. Since bio-impedance measurements involve applying electricity to the skin of the patient, such measurements are poorly tolerated by patients due to skin irritation. Further, the measured signals vary greatly.

U.S. Pat. No. 7,074,193 (to Satoh et al.) and U.S. Pat. No. 7,291,113 (to Satoh et al.) which are incorporated herein by reference in their entirety, describe a method and apparatus for extracting components from a measured pulse wave of blood pressure using a fourth order derivative and an n-th order derivative, respectively.

A clinical need exists for a system and method that are inexpensive, easy to perform, non-invasive, well tolerated by patients, and provide an indication of the ability of arteries to respond to an increase in blood flow.

SUMMARY

A method and diagnostic system provide for assessing changes in arterial volume of a limb segment of a mammal. In one aspect, the diagnostic system determines amplitudes of component pulse waves of detected volume pulse waves of a limb segment detected during a baseline period to determine a baseline arterial volume of the limb segment. The diagnostic system determines amplitudes of component pulse waves of detected volume pulse waves of the limb segment detected during a time period after a stimulus has been applied to the mammal to induce a period of change in the arterial volume of the limb segment. The diagnostic system determines relative change in arterial volume of the limb segment during the time period after the stimulus relative to the arterial volume of the limb during the baseline period from the amplitudes of the component pulse waves of the detected volume pulse waves at baseline and after the stimulus.

In another aspect, the diagnostic system determines relative change in arterial volume by comparing the amplitudes of the component pulse waves of volume pulse waves at baseline and after the stimulus.

In another aspect, the component pulse wave is an early systolic component. In another aspect, the diagnostic system determines relative change in arterial volume by comparing maximum amplitudes of the early systolic components of the volume pulse waves during the baseline period and maximum amplitudes of the early systolic components of the volume pulse waves after the stimulus.

In another aspect, the diagnostic system monitors the limb segment to detect the detected volume pulse waves of the limb segment during the baseline period, and monitors the limb segment to detect the detected volume pulse waves of the limb segment during an after-stimulus period.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

DETAILED DESCRIPTION

A preferred embodiment of the present invention is now described with reference to the figures where like reference numbers indicate identical or functionally similar elements. Also in the figures, the leftmost digits of each reference number correspond to the figure in which the reference number is first used.

Figure 1:
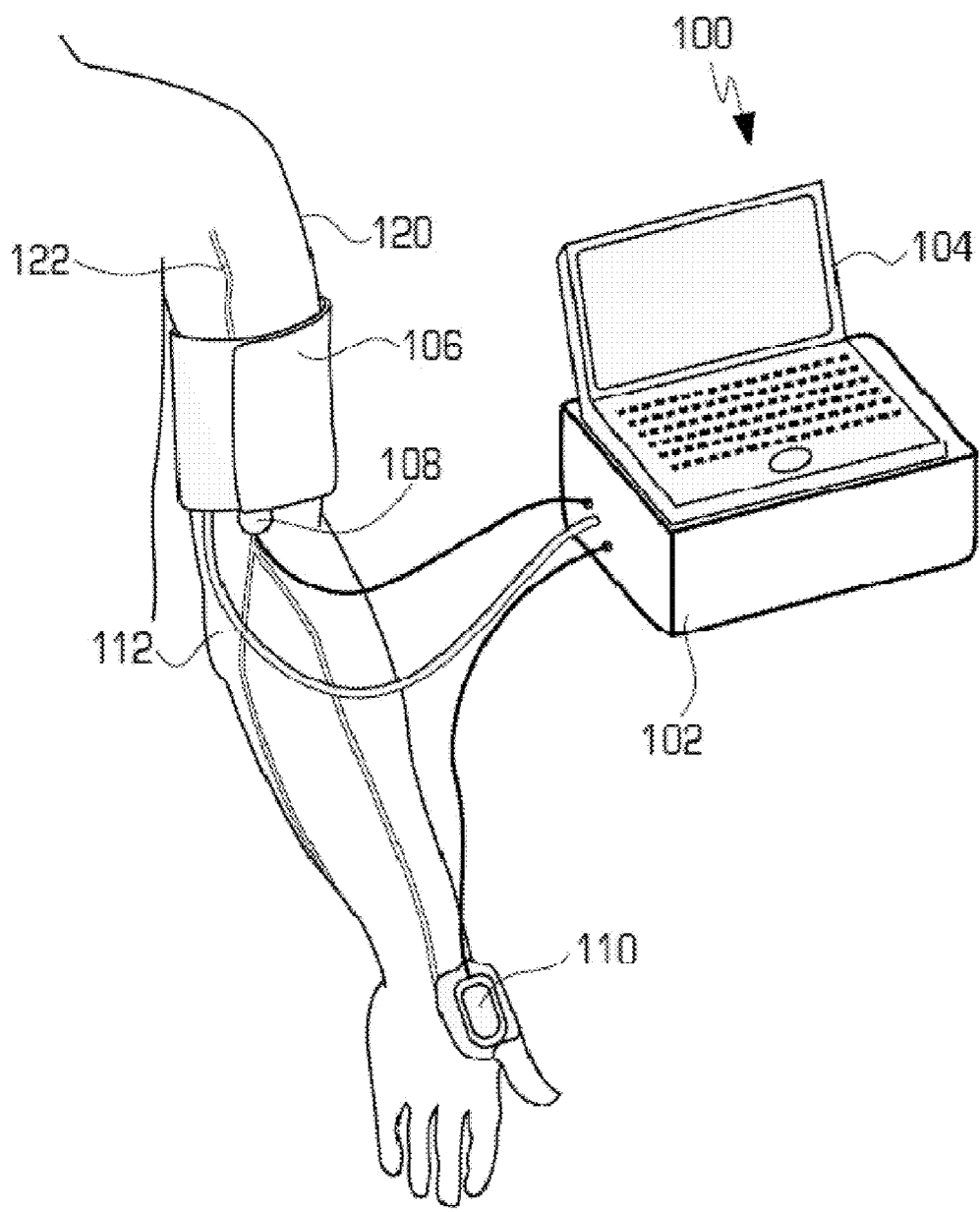
FIG. 1 is a pictorial diagram illustrating a diagnostic system in accordance with the present invention.

FIG. 1 is a pictorial diagram illustrating a diagnostic system 100 in accordance with the present invention. The diagnostic system 100 comprises a diagnostic device 102, a diagnostic computer 104, a cuff 106, a Doppler transducer 108, and an oxygen saturation ($StO_2$) sensor 110.

As used herein, the volume pulse waves are oscillations in the blood pressure between the systolic and the diastolic pressures of arteries. The diagnostic system 100 detects the volume pulse waves and performs diagnostics for assessing arterial volume changes of a limb segment based on the detected pulse waves. In some embodiments, the volume pulse wave includes a composite pulse wave formed of a superposition of a plurality of component pulse waves. The component pulse waves partially overlap and the arterial pulse wave shape or contour is formed by the superposition of the component pulse waves. The component pulse waves may include, for example, an incident systolic wave (also called early systolic wave), a reflected wave (also called late systolic wave), and other waves. The diagnostic system 100 measures amplitudes of components of arterial volume pulse waves as a way of monitoring the changes in arterial volume of the limb segment after a stimulus. While it may be easier to measure the amplitude of the whole arterial volume pulse wave, the timing of the component pulse waves shifts throughout the testing procedure and changes the shape of the pulse wave. In some embodiments, the diagnostic system 100 measures amplitude of a physiologically significant component (such as a component pulse wave) of the volume pulse wave to assess the changes in arterial volume of the limb segment. The diagnostic system 100 may use any component pulse wave of the detected volume pulse wave or portion thereof (such as maximum, inflection point, or amplitude at a fixed time of the component pulse wave), any portion of the volume pulse wave (such as maximum, inflection point, or amplitude at a fixed time of the volume pulse wave), or a combination thereof for the diagnostics for assessing arterial volume changes. As an illustrative example, the operation of the diagnostic system 100 is described herein in terms of the early systolic wave.

In use, the cuff 106 is disposed around a limb 120 so that when the cuff 106 is inflated, the cuff 106 constricts a segment of the limb 120. It is understood by those skilled in the art that the measurements of the changes in the arterial volume of a limb segment described herein are not measuring the volume changes of only a single artery in the limb 120, but are measuring the volume changes in substantially all arteries in the segment of the limb 120 that is being constricted. Although the volume changes measurements and the physiology thereof are described for a single artery, one skilled in the art will recognize that the invention is not restricted to a single artery and that the volume changes measurements are of all or substantially all arteries in the segment of the limb being measured. The limb 120 may be any limb or digits thereof, but for the sake of simplicity, the limb 120 is described as an arm, and the artery that is being evaluated is described as the brachial artery. In some embodiments, the limb 120 is a leg and the artery is a femoral artery. Although the diagnostic system 100 is described for use on a human being, the invention is not so limited. The diagnostic system 100 can be used on other mammals.

The diagnostic computer 104 provides control signals to the diagnostic device 102 and receives information and detected data from the diagnostic device 102.

The diagnostic device 102 provides air to and releases air from the cuff 106 via a tube 112 of the cuff 106. The diagnostic device 102 may control, detect and monitor the air pressure in the tube 112. In some embodiments, a gas other than air, or a liquid, such as water, may be used in the cuff 106, the tube 112, and the pneumatic module 202 (see FIG. 2). In some embodiments, the cuff can be an electrically-controlled elastomer or a mechanically-controlled material.

Although the diagnostic system 100 is described herein as applying a pressure via the cuff 106 to the limb 120 to occlude an artery 122 as a stimulus of the endothelium as blood flows into the artery 122 after release of the occlusion, other forms of stimuli may be provided. In various embodiments, the stimulus of the endothelium comprises a mechanical stimulation, a thermal stimulation, a chemical stimulation, an electrical stimulation, a neurological stimulation, a mental stimulation or a stimulation via physical exercise, or any combination thereof, to induce a change in arterial volume of the limb segment. The stimuli are well known and some of them induce formation of nitric oxide by the endothelial cells lining the walls of the arteries. In some embodiments, the stimulus to the endothelium can also be delivered in any way that transiently and locally increases the blood flow and shear stress at the arterial wall. For instance, this can be achieved by applying ultrasound waves such that it creates turbulence inside a major artery. The chemical stimulation may be, for example, a vasoactive agent, such as an oral administration of nitroglycerol, or an intra-brachial infusion of acetylcholine.

The diagnostic device 102 provides control signals to and receives measurement signals from the Doppler transducer 108 and the oxygen saturation ($StO_2$) sensor 110. The Doppler transducer 108 and the oxygen saturation ($StO_2$) sensor 110 are used in some embodiments for the purpose of quantifying the amount of a vasodilatory stimulus, such as a transient occlusion of the arteries of the limb segment.

The Doppler transducer 108 is disposed on the limb 120 and adjacent to the artery 122 in the limb 120 and distal or proximal from the cuff 106 for measuring blood flow velocity in the artery 122 using a Doppler process. The Doppler transducer 108 may be any conventional Doppler transducer designed to measure blood flow velocity in a conduit artery. In some embodiments, the diagnostic system 100 does not include a Doppler transducer 108.

The oxygen saturation ($StO_2$) sensor 110 is disposed on the limb 120 and distal from the cuff 106 for measuring oxygen levels in the tissue of the limb to determine the extent to which hemoglobin in the tissue is saturated with oxygen. The oxygen saturation ($StO_2$) sensor 110 may be any conventional $StO_2$ sensor. In some embodiments, the diagnostic system 100 does not include an oxygen saturation ($StO_2$) sensor 110.

Although the Doppler transducer 108 and the oxygen saturation sensor 110 are described herein as an apparatus to quantify the amount of stimulus via occlusion, other apparatus to quantify the amount of vasoactive stimuli may be provided.

Although the diagnostic computer 104 is described herein as performing the control, computation, and analysis of the diagnostic system 100, the invention is not so limited. The diagnostic device 102 may include a processor or microcontroller for performing any or all of the operations described herein as being performed by the diagnostic computer 104.

Although the diagnostic computer 104 is described herein as being local to the blood diagnostic device 102, the diagnostic computer 104 may be coupled to the diagnostic device 102 through a communication line, system, or network, such as the Internet, wireless, or landline. For example, the operation of the diagnostic device 102 may be done near the patient while the diagnostic computer 104 may remotely process the data.

Figure 2:
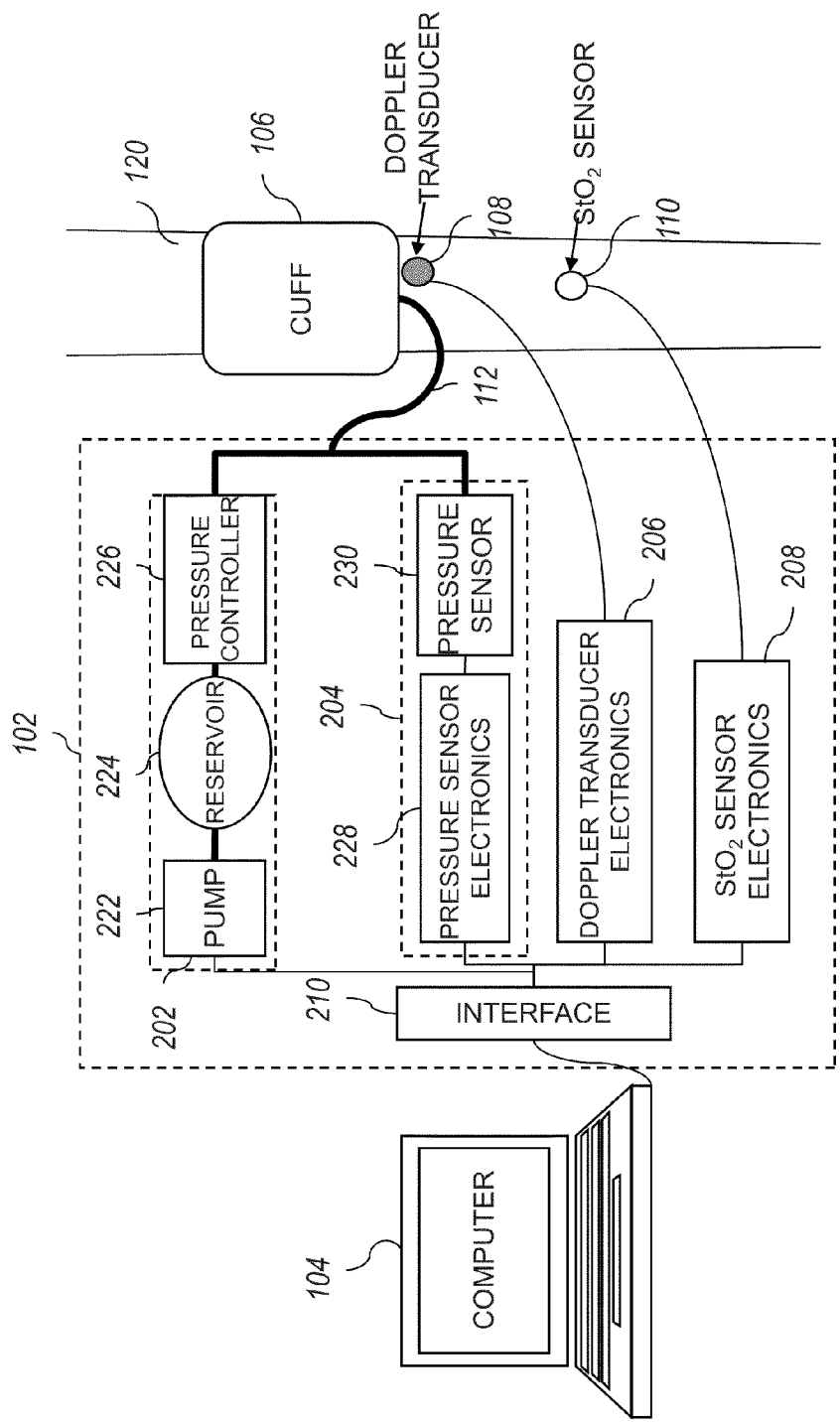
FIG. 2 is a block diagram illustrating the diagnostic system of FIG. 1.

FIG. 2 is a block diagram illustrating the diagnostic device 102. The diagnostic device 102 comprises a pneumatic module 202, a pressure detector 204, a Doppler transducer system 206, an oxygen saturation ($StO_2$) sensor system 208, and an interface 210. The pneumatic module 202 controls pressure in the cuff 106 in response to control signals from the diagnostic computer 104. The pneumatic module 202 comprises a pump 222 (e.g., an air pump) for pressurizing air, a reservoir 224 for storing the pressurized air, and a pressure controller 226 for controlling the release of air via the tube 112 into the cuff 106.

The pressure detector 204 comprises a pressure sensor electronics system 228 for controlling a pressure sensor 230, which senses pressure in the cuff 106 via the tube 112. The pressure sensor 230 detects pressure oscillations in the cuff 106 resulting from pulse waves in the artery 122. In some embodiments, the pressure sensor 230 is disposed in the cuff 106 or in the tube 112. In some embodiments, the pressure sensor 230 is a plethysmography sensor, such as a reflective photo-plethysmography sensor.

The interface 210 communicates control signals and information signals between the diagnostic computer 104 and the pneumatic module 202, the pressure detector 204, the Doppler transducer system 206, and the oxygen saturation ($StO_2$) sensor system 208. The interface 210 may include a processor or microcontroller for performing any or all of the operations described herein.

The Doppler transducer system 206 communicates with the Doppler transducer 108 for measuring blood flow velocity in the artery 122. In some embodiments, the diagnostic computer 104 commands the Doppler transducer system 206 to measure blood flow velocity through the artery 122 after the cuff pressure has been released to assess the amount of stimulus delivered via shear stress to the artery 122.

In some embodiments, the diagnostic computer 104 may include test data of blood velocity and may use such test data to quantify the amount of the post-occlusion stimulus in a patient. The diagnostic computer 104 may use this data as part of the assessment of changes in the arterial volume of the limb segment described herein.

The oxygen saturation ($StO_2$) sensor system 208 communicates with the oxygen saturation ($StO_2$) sensor 110 to measure oxygen levels in the tissue for determining the extent to which the hemoglobin in the blood of the tissue is saturated with oxygen.

In some embodiments, the diagnostic computer 104 may include test data of oxygen saturation and may use such test data to standardize the degree of limb ischemia among the test subjects, and quantify the amount of the post-occlusion stimulus in a particular patient. The diagnostic computer 104 may use this data as part of the assessment of changes in the arterial volume of the limb segment described herein.

Figure 3:
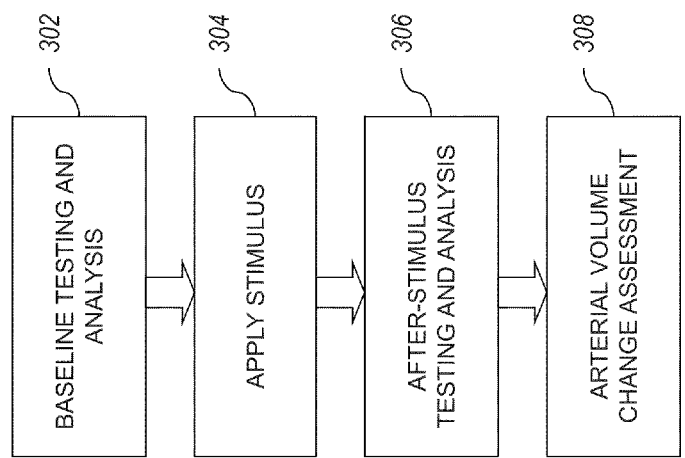
FIG. 3 is a flow chart illustrating an operation of arterial volume change assessment of the diagnostic system of FIG. 1.

FIG. 3 is a flow chart illustrating an operation of arterial volume change assessment of the diagnostic system 100. Before operating the diagnostic system 100, the cuff 106 is placed around the limb 120 (e.g., arm) of the patient. The test is started with an entry on the diagnostic computer 104 in any well known manner such as keystrokes on a keyboard (not shown) or movement of a cursor and selection of a screen button via a mouse (not shown). In response to an initiation of the diagnostic command, the diagnostic computer 104 assesses changes in the arterial volume of a segment of the limb 120. The diagnostic computer 104 performs baseline testing and analysis (block 302) during a baseline period 402 (see FIG. 4 below). In some embodiments, the diagnostic system 100 detects and analyzes volume pulse waves of a segment of the limb 120 during the baseline period in which no stimulus is applied to the patient. In some embodiments, the analysis of the volume pulse waves includes determining amplitudes of the detected volume pulse waves to calculate a baseline arterial volume of the segment of the limb 120. One embodiment of the baseline testing is described below in conjunction with FIG. 4.

A stimulus is applied to the patient to induce a period of change in arterial volume of the segment of the limb 120 (block 304) during a stimulus period 404 (see FIG. 4 below). In some embodiments, the diagnostic computer 104 commands the pneumatic module 202 to pressurize the cuff 106 to a level sufficient to occlude the artery 122. In some embodiments, the cuff 106 is inflated to a pressure above systolic for a period of time sufficient to induce change in arterial volume of the segment of the limb 120 after releasing the cuff pressure.

The diagnostic computer 104 performs after-stimulus testing and analysis (block 306) during an after-stimulus period 406 (see FIG. 4 below). In some embodiments, the diagnostic system 100 detects and analyzes volume pulse waves of a segment of the limb 120 after the stimulus, such as a predetermined time after either starting or terminating the application of the stimulus. In some embodiments, the analysis of the volume pulse waves includes determining amplitudes of early systolic components of the detected volume pulse waves to calculate an after-stimulus arterial volume of the segment of the limb 120. One embodiment of the after-stimulus testing is described below in conjunction with FIG. 4. The analyses of blocks 302 and 306 may be performed separately from the testing and at a later time.

The diagnostic computer 104 performs an arterial volume change assessment (block 308). In some embodiments, the diagnostic computer 104 calculates the relative change in arterial volume of the limb 120 during the after-stimulus time period 406 (see FIG. 4 relative to the arterial volume of the limb 120 during the baseline period 402 (see FIG. 4) from the amplitudes of the early systolic component of volume pulse waves at baseline and after the stimulus. One embodiment of the arterial volume change assessment is described below in conjunction with FIG. 15.

In some embodiments, the assessment of the level of hypoxemia (or oxygen saturation) can be included in the arterial volume change assessment (block 308) and achieved by any method that is compatible with the testing procedure (e.g., based on non-pulsatile measurements of hypoxemia if a cuff 106 is used to occlude the artery). In some embodiments, the assessment of post-occlusion blood velocity or blood shear stress can be included in the arterial volume change assessment (block 308) and achieved by any method that is compatible with the testing procedure (e.g., based on Doppler measurements).

Figure 4:
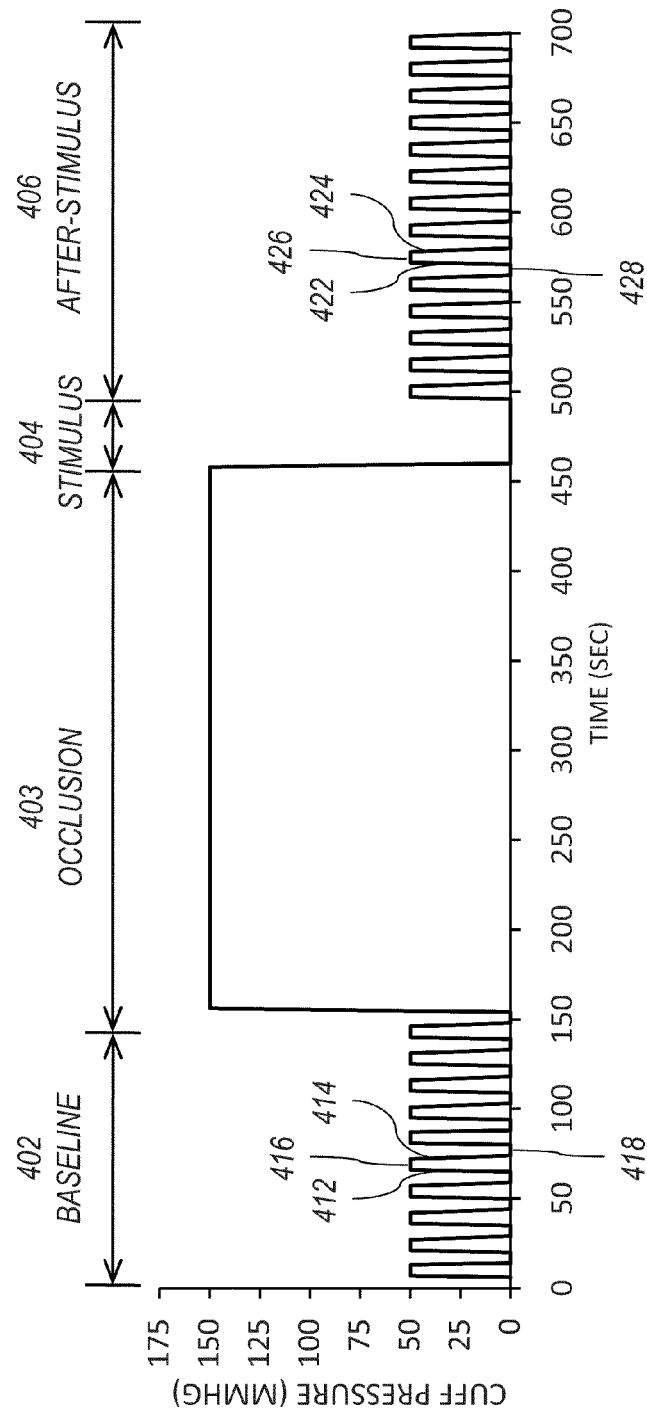
FIG. 4 is a timing diagram illustrating pressure applied to a limb during baseline testing and analysis and after-stimulus testing and analysis of FIG. 3 with an occlusion providing a stimulus.

FIG. 4 is a timing diagram illustrating pressure applied to the limb 120 during the baseline testing and analysis (block 302) and after-stimulus testing and analysis (block 306) of FIG. 3 with an occlusion providing a stimulus. Prior to the procedure described in FIG. 4, a patient's blood pressure is measured to select an individualized pressure that will be applied to the limb. During blood pressure measurements, the diagnostic system 100 determines systolic, diastolic, and mean arterial pressures, which may be done in a conventional manner. Once the blood pressure measurements are performed, the individualized pressure applied to the patient's limb is determined as a percentage of diastolic, or systolic, or mean arterial pressure. It can also be determined according to a formula based on the patient's blood pressure. For instance, the pressure applied to the patient's limb may be computed as the patient's diastolic pressure minus 10 mm Hg. Standardization of the pressure applied to each patient allows the comparison of the test data among patients in whom blood pressures are different.

As an illustrative example, during a baseline period 402 (e.g., 150 seconds), the diagnostic device 102 measures the resting arterial volume pulse waves of the brachial artery 122, which are indicative of the resting diameter of the brachial artery 122. During the baseline period 402, the diagnostic system 100 commands the diagnostic device 102 to perform a series of rapid inflations 412 and deflations 414 of the cuff 106, and to collect data from the pressure sensor 230. (For the sake of clarity, only ten inflations 412 and ten deflations 414 are shown, but other numbers may be used. For the sake of clarity only one inflation/deflation cycle is labeled.) In each cycle, the cuff is rapidly inflated 412 to a pressure, such as the sub-diastolic arterial pressure, and held inflated 416 for a predetermined time (e.g., 4 to 6 seconds) and then held deflated 418 for a predetermined time (e.g., 4 to 10 seconds). In some embodiments, the diagnostic computer 104 may dynamically determine the time of the inflation 416 and the number of pulses based on the measurements. While the cuff 106 is inflated 416, the diagnostic device 102 detects a plurality of pressure oscillations (or volume pulse waves).

After the baseline period 402, the diagnostic device 102 inflates the cuff 106 to a supra-systolic pressure (e.g., systolic pressure plus 50 mm Hg) to temporarily occlude the artery 122 for an occlusion period 403 (e.g., about 300 seconds). Concurrent with the occlusion, the oxygen saturation ($StO_2$) sensor electronics 208 controls the oxygen saturation ($StO_2$) sensor 110 to monitor the level of hypoxemia in the limb distal to the occluding cuff.

Thereafter, the diagnostic device 102 rapidly deflates the cuff 106 (e.g., to a pressure below venous pressure, for instance, below 10 mm Hg) to allow the blood flow to rush into the limb 120 during a stimulus period 404. The pressure release of the cuff 106 creates a rapid increase in the blood flow in the artery 122, which generates shear stress on the endothelium of the brachial artery 122. The shear stress stimulates the endothelial cells to produce nitric oxide (NO), which dilates the artery 122.

Concurrent with the cuff deflation, the Doppler transducer electronics 206 controls the Doppler transducer 108 to collect data for a predetermined time (e.g., 10-180 seconds) during which time the Doppler transducer 108 measures blood velocity.

During an after-stimulus period 406, the diagnostic system 100 commands the diagnostic device 102 to perform a series of rapid inflations 422 and deflations 424 of the cuff 106, and to collect data from the pressure sensor 230 in a manner similar to that for the baseline period 402 for a predetermined time (e.g., 1-10 minutes). (For the sake of clarity, only fourteen inflations 422 and fourteen deflations 424 are shown, but other numbers may be used. For the sake of clarity only one inflation/deflation cycle is labeled.) In each series, the cuff is rapidly inflated to a pressure, and held inflated 426 for a predetermined time (e.g., 4 to 6 seconds), and then deflated 428. In some embodiments, the diagnostic computer 104 may dynamically determine the time of the inflation 426 and the number of pulses detected based on the measurements. During this time, the diagnostic computer 104 monitors the dynamics of changes in arterial volume of a limb segment (a gradual increase in pulse wave amplitude to maximum and then a gradual decrease in the pulse wave amplitude to return to a resting state).

Figure 5:
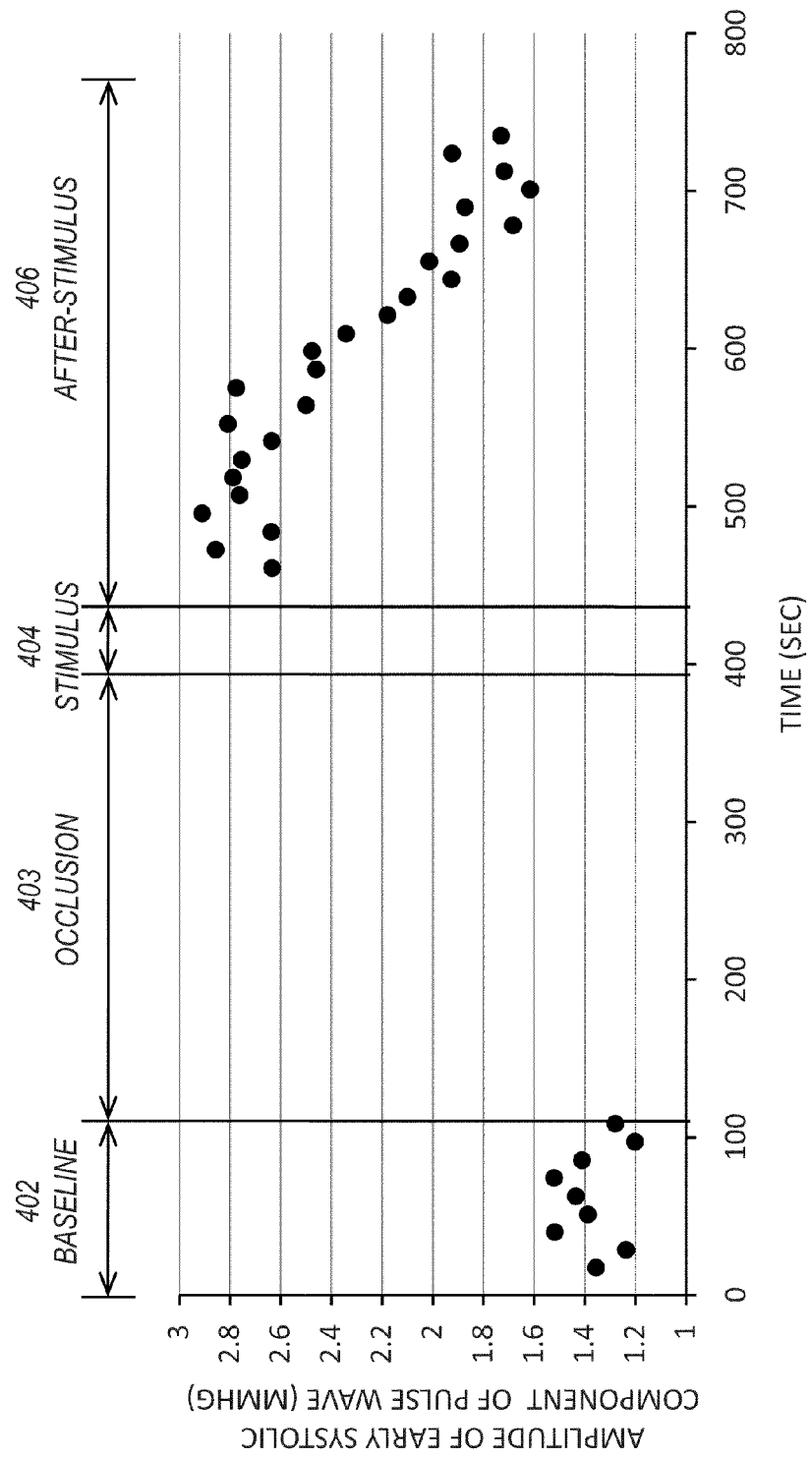
FIG. 5 is a timing diagram illustrating amplitudes of early systolic components of pulse waves measured during a baseline period and an after-stimulus period of FIG. 4.

FIG. 5 is a timing diagram illustrating amplitudes of early systolic components of pulse waves measured during the baseline period 402 and the after-stimulus period 406 of FIG. 4.

Figure 6:
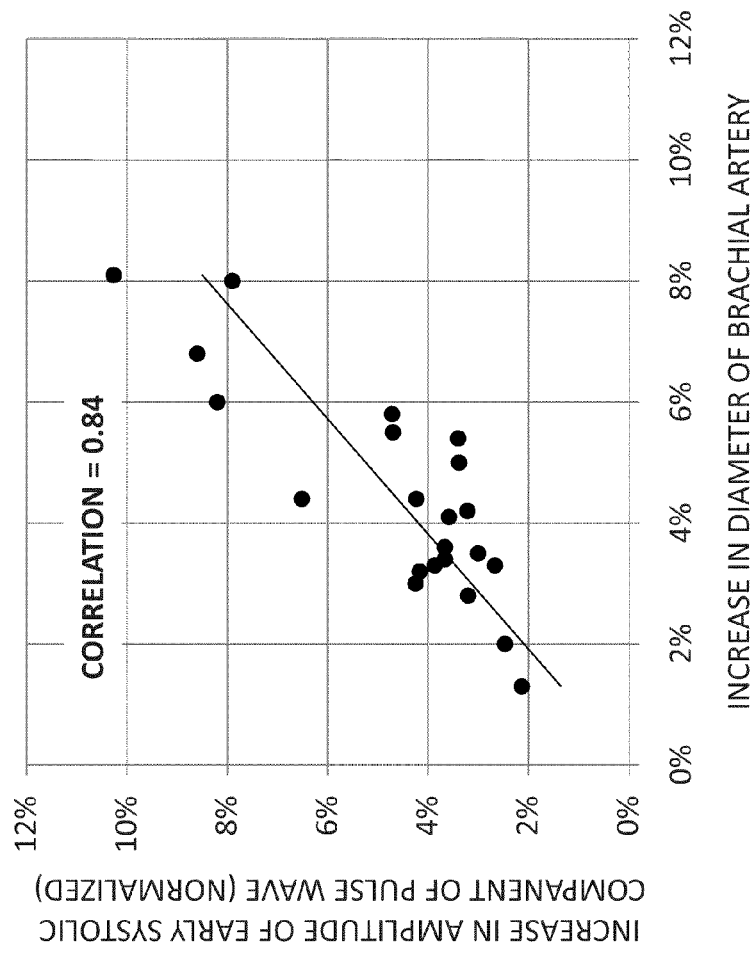
FIG. 6 is a graph illustrating correlation between the normalized increases in amplitudes of early systolic components of pulse waves of a segment of an arm as measured in some embodiments and the increases in diameter of the brachial artery measured via ultrasound imaging of the brachial artery.

FIG. 6 is a graph illustrating correlation between the normalized increases in amplitudes of early systolic components of volume pulse waves of a segment of an arm as measured in some embodiments and the increases in diameter of a brachial artery measured via ultrasound imaging of the brachial artery. Each data point in the graph corresponds to a different patient. The stimulus in both methods was a 5-minute occlusion of the brachial artery via cuff inflation to a supra-systolic pressure. A normalization of the test results obtained with the present invention accounts for the fact the diagnostic system 100 assesses the change in the volume of substantially all arteries in the limb segment, while the ultrasound imaging visualizes only the main artery.

Figure 7:
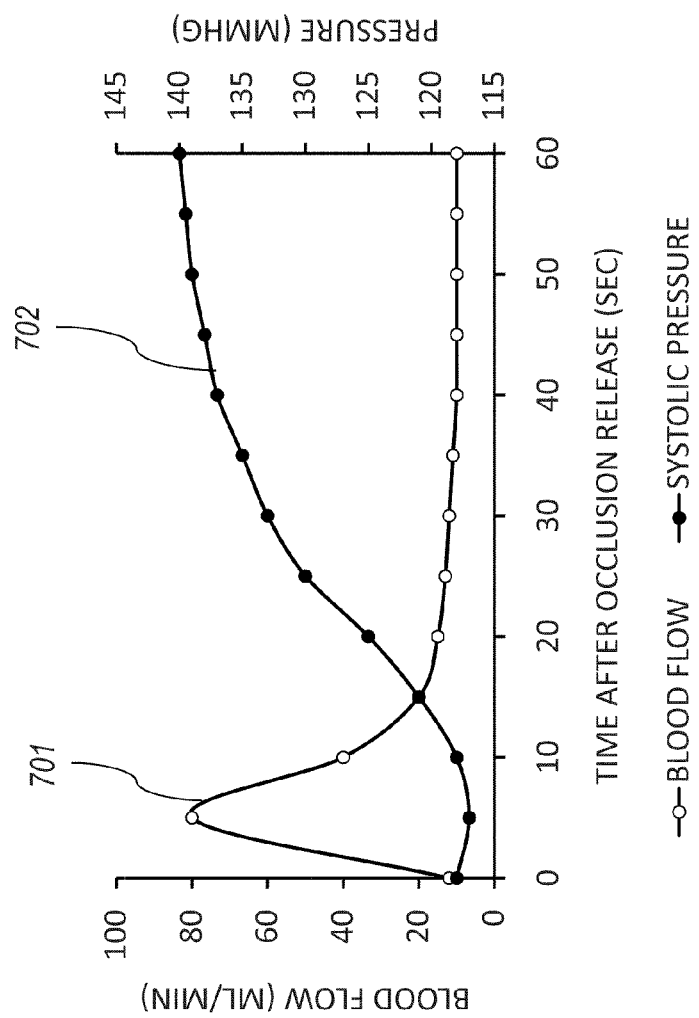
FIG. 7 is a timing diagram illustrating blood flow and systolic pressure after release of the occlusion in FIG. 4.

FIG. 7 is a timing diagram illustrating blood flow and systolic pressure after release of the occlusion in FIG. 4 during the stimulus period 404. A line 701 shows a rapid increase in blood flow followed by a decrease to normal flow. A line 702 shows the temporary drop in systolic pressure after the occlusion.

Figure 8B:
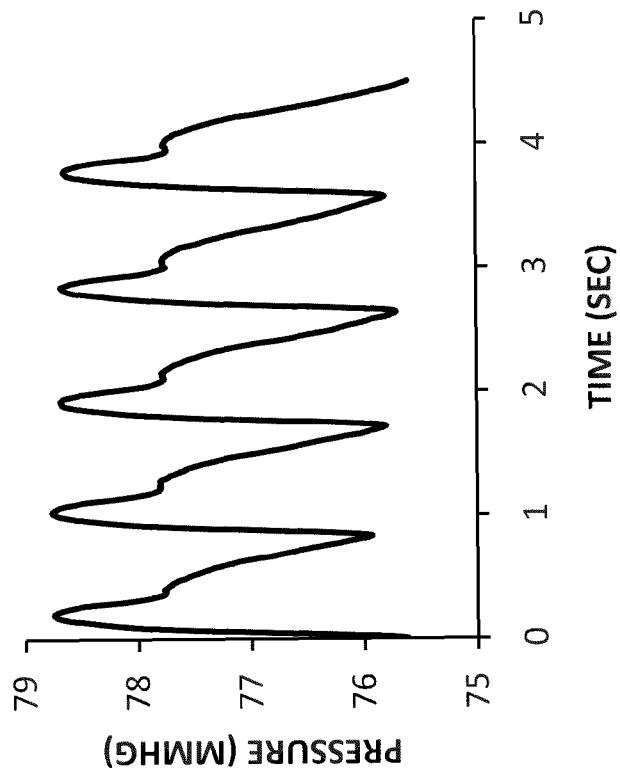
FIGS. 8a and 8b are timing diagrams illustrating, in an expanded view, measured cuff pressure oscillations of a limb during one inflation/deflation cycle of FIG. 4 before occlusion and during one cycle of FIG. 4, respectively, after occlusion of blood vessels in the limb.
Figure 8A:
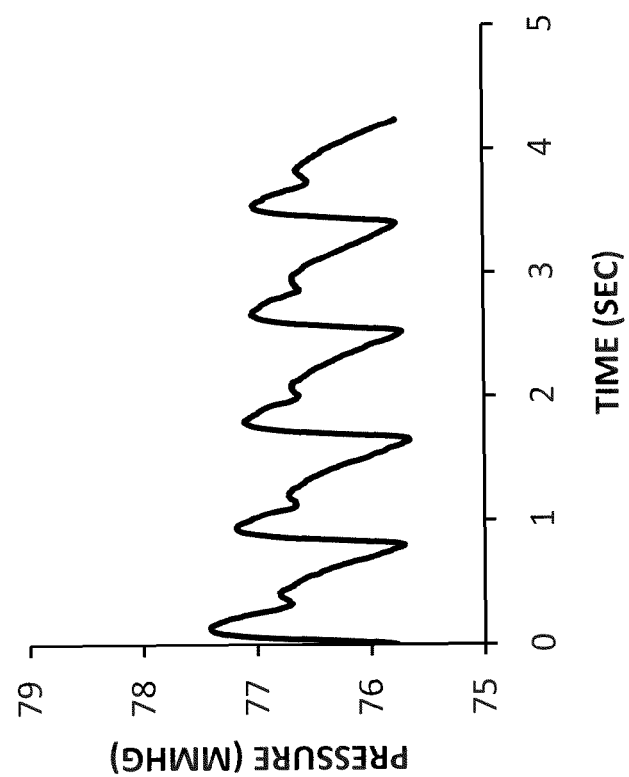

FIGS. 8a and 8b are timing diagrams illustrating measured cuff pressure oscillations of the limb 120 during one inflation/deflation cycle before occlusion (FIG. 8a) and during one cycle after occlusion (FIG. 8b) of blood vessels in the limb 120 in an expanded view. During the cuff pressure sequence, data is collected about the oscillations in the cuff pressure due to the pulsation of the brachial artery. The changes in the oscillatory amplitude (or the amplitude of a pulse wave) are related to the changes in the radius of the brachial artery, and FIG. 8b shows the pulse wave amplitude after occlusion being larger than the pulse wave amplitude before occlusion.

In some embodiments, arterial volume pulse waves are detected using an external pressure that is applied to the segment of the limb 120. In some embodiments, the externally applied pressure varies gradually between near-systolic and near-diastolic. In some embodiments, the external pressure is applied by initially applying the external pressure at a pressure near systolic, and gradually reducing the external pressure to a pressure near diastolic. In some embodiments, the external pressure is applied by initially applying the external pressure at a pressure near diastolic, gradually increasing to a pressure near systolic at a rate to allow the oscillations to be detected, and then quickly decreasing the pressure.

Figure 9:
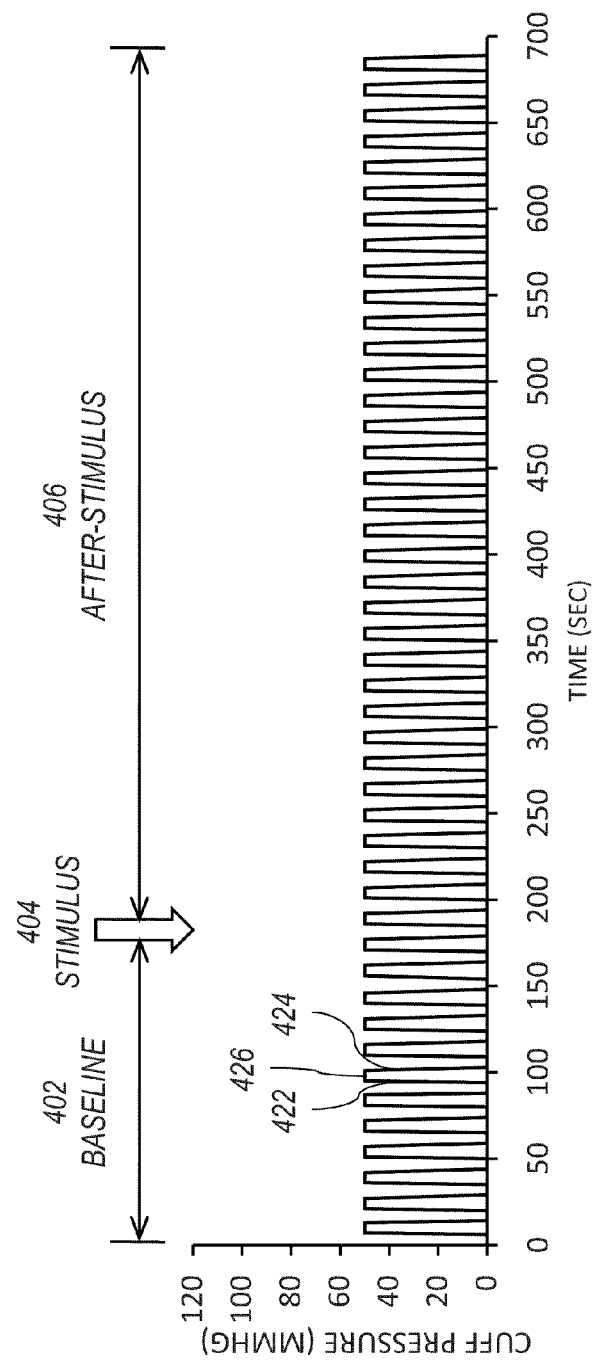
FIG. 9 is a timing diagram illustrating pressure applied to the limb during the baseline testing and analysis and after-stimulus testing and analysis of FIG. 3 with an oral administration of nitroglycerin providing a stimulus.

In some embodiments, as shown in FIGS. 4 and 9, an applied external pressure is cycled between a high level and a low level so that the arterial volume pulse waves are determined while the external pressure is at the high level. In some embodiments, the high level is below diastolic pressure and the low level is below venous pressure.

In some embodiments, the high level 416 or 426 is maintained for no more than 10 seconds in any cycle. In some embodiments, the low level 418 or 428 is maintained for at least 4 seconds in any cycle. In some embodiments, the measurements are taken over at least one cardiac cycle.

FIG. 9 is a timing diagram illustrating pressure applied to the limb 120 during the baseline testing and analysis (block 302) and after-stimulus testing and analysis (block 306) of FIG. 3 with an oral administration of nitroglycerin providing a stimulus. Because there is no occlusion period 403, the diagnostic system 100 generates a series of rapid inflations 422 and deflations 424 with an inflation state 426 and measures the volume pulse waves during the baseline period 402, the stimulus period 404 and the after-stimulus period 406.

Figure 10:
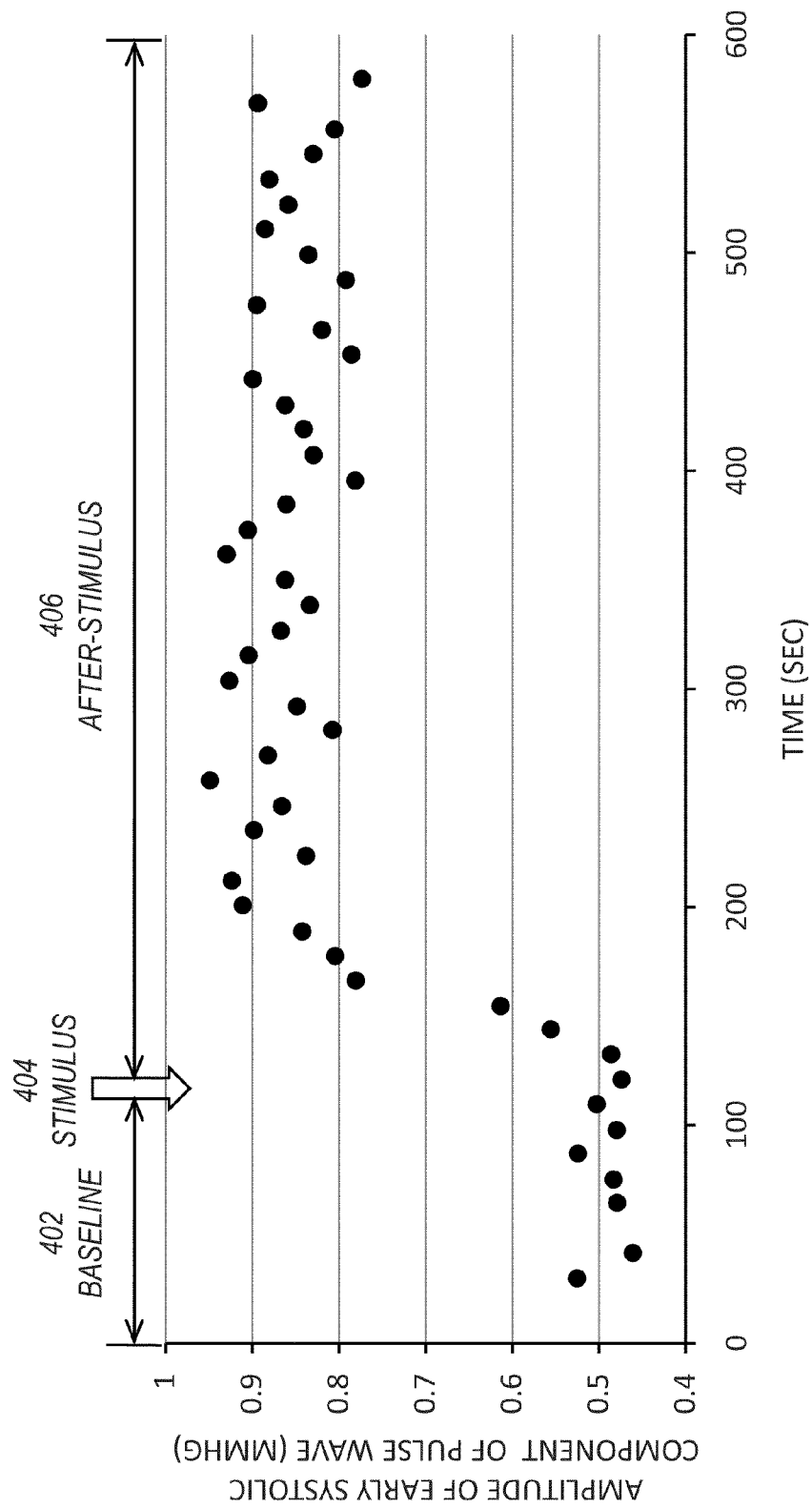
FIG. 10 is a timing diagram illustrating amplitudes of early systolic components of pulse waves measured during a baseline period, a stimulus period, and a after-stimulus period of FIG. 9.

FIG. 10 is a timing diagram illustrating amplitudes of early systolic components of pulse waves measured during the baseline period 402, the stimulus period 404 and the after-stimulus period 406 of FIG. 9.

Figure 11:
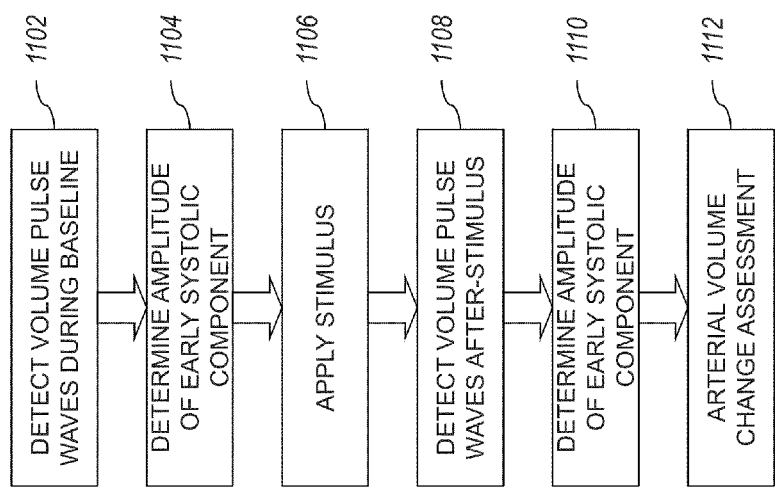
FIG. 11 is a flow chart illustrating one embodiment of the operation of arterial volume change assessment of FIG. 3.

FIG. 11 is a flow chart illustrating one embodiment of the operation of arterial volume change assessment (block 308 of FIG. 3). In response to an initiation of the diagnostic command from the user, the diagnostic computer 104 assesses change in the arterial volume of a segment of the limb 120. The diagnostic device 102 detects volume pulse waves of a segment of the limb during the baseline period 402, such as described above in conjunction with FIGS. 4-8 (or FIGS. 9-10, depending on the stimulus) (block 1102). In some embodiments, the diagnostic computer 104 commands the pneumatic module 202 to pressurize the cuff 106 to a level sufficient for the pressure detector 204 to detect volume pulse waves of a segment of the limb 120.

The diagnostic device 102 determines amplitudes of early systolic components of the detected volume pulse waves (block 1104). In some embodiments, the diagnostic computer 104 commands the pressure detector 204 to detect volume pulse waves of the segment of the limb 120. The diagnostic computer 104 analyzes the waveforms of the detected volume pulse waves and determines relevant amplitudes of the volume pulse waves for the baseline period. In one embodiment, the relevant amplitude of a pulse wave is the difference between the maximum and the minimum pressures of the pulse wave. In some embodiments, the relevant amplitude is the amplitude of the early systolic component. One embodiment for determining amplitudes of block 1104 is described below in conjunction with FIG. 12. (Blocks 1102 and 1104 may be used for the block 302 of FIG. 3).

The diagnostic device 102 applies a stimulus during the stimulus period 402 to induce a period of change in arterial volume of the segment of the limb 120 (block 1106). In some embodiments, the diagnostic computer 104 commands the pneumatic module 202 to pressurize the cuff 106 to a level sufficient for occluding the artery 122. (Block 1106 may be used for the block 306 of FIG. 3; other examples of stimuli are described above in conjunction with FIG. 1 and FIGS. 9-10).

The diagnostic device 102 detects volume pulse waves of the segment of the limb 120 during the after-stimulus period 406 to detect change in arterial volume of a limb segment, such as described above in conjunction with FIGS. 4-8 (block 1108). In some embodiments, the diagnostic computer 104 commands the pneumatic module 202 to pressurize the cuff 106 to a level sufficient for the pressure detector 204 to detect volume pulse waves of a segment of the limb 120.

The diagnostic device 102 determines amplitudes of early systolic components of the detected volume pulse waves after the stimulus (block 1110). In some embodiments, the diagnostic computer 104 commands the pressure detector 204 to detect volume pulse waves of the segment of the limb 120. The diagnostic computer 104 analyzes the waveforms of the detected volume pulse waves and determines relevant amplitudes of the volume pulse waves for the baseline period. In one embodiment, the relevant amplitude of a pulse wave is the difference between the maximum and the minimum pressures of the pulse wave. In some embodiments, the relevant amplitude is the amplitude of the early systolic component. One embodiment for determining amplitudes of block 1110 is described below in conjunction with FIG. 12. (Blocks 1108 and 1110 may be used for the block 306 of FIG. 3).

The diagnostic device 102 performs an arterial volume change assessment (block 1112). In some embodiments, the diagnostic computer 104 calculates the relative change in arterial volume of the limb segment 120 during the after-stimulus time period 406 relative to the arterial volume of the limb 120 during the baseline period 402 from the amplitudes of the early systolic component of volume pulse waves at baseline and after the stimulus. In some embodiments, the diagnostic computer 104 calculates the relative change by comparing the amplitudes of early systolic component of volume pulse waves at baseline (block 1104) and after the stimulus (block 1106). (Block 1112 may be used for the block 308 of FIG. 3). One embodiment of the arterial volume change assessment is described below in conjunction with FIG. 15.

Figure 12:
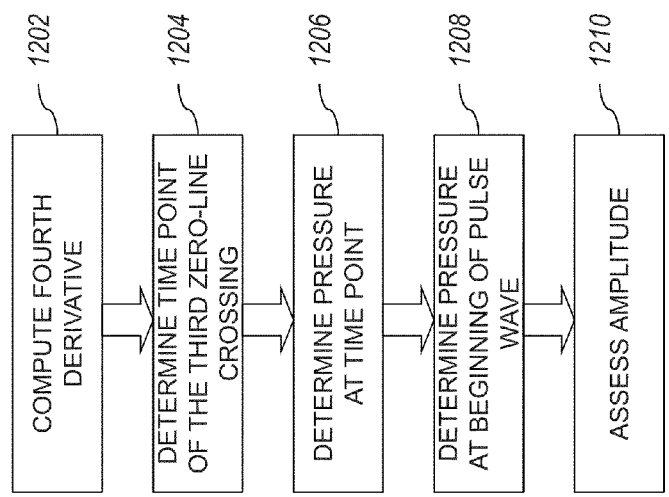
FIG. 12 is a flow chart illustrating one embodiment of an operation of determining amplitude of the arterial volume change assessments of FIGS. 3 and 11.

FIG. 12 is a flow chart illustrating one embodiment of an operation of determining amplitude of the arterial volume change assessments (block 308 of FIG. 3 and block 1112 of FIG. 11). The diagnostic computer 104 determines the amplitude of the early systolic component of a volume pulse wave by computing fourth derivative of the detected volume pulse wave (block 1202). The diagnostic computer 104 determines a time at which the fourth derivative crosses the zero-line for the third time (block 1204). (A third zero-line crossing 1322 of FIG. 13 below and a third zero-line crossing 1422 of FIG. 14 below.) In some embodiments, the diagnostic computer 104 may instead determine the second derivative of the detected volume pulse wave. In some embodiments, the diagnostic computer 104 may instead determine an inflection point in the volume pulse wave and use the time of occurrence of the inflection point. In some embodiments, the diagnostic computer 104 may instead use Fourier transformation of the volume pulse wave to determine the time of occurrence of the peaks of the pulse component pulse waves.

The diagnostic computer 104 determines a pressure value on the detected volume pulse wave at that time (block 1206). The diagnostic computer 104 determines a pressure value at the beginning of the volume pulse wave (block 1208). In some embodiments, the diagnostic computer 104 determines the pressure value at the beginning of the volume pulse wave by determining a minimum during the diastolic component of the pulse wave. The diagnostic computer 104 assesses the amplitude of the early systolic component of the volume pulse wave as the difference between the pressure values (block 1210).

In some embodiments, the diagnostic computer 104 may compute other orders of derivatives in block 1202, or not compute a derivative, but instead determine the inflection point corresponding to the peak of the early systolic component of the pulse wave by other methods. In other embodiments, the diagnostic computer 104 may determine the maximum amplitude of the arterial volume pulse waves.

Figure 13:
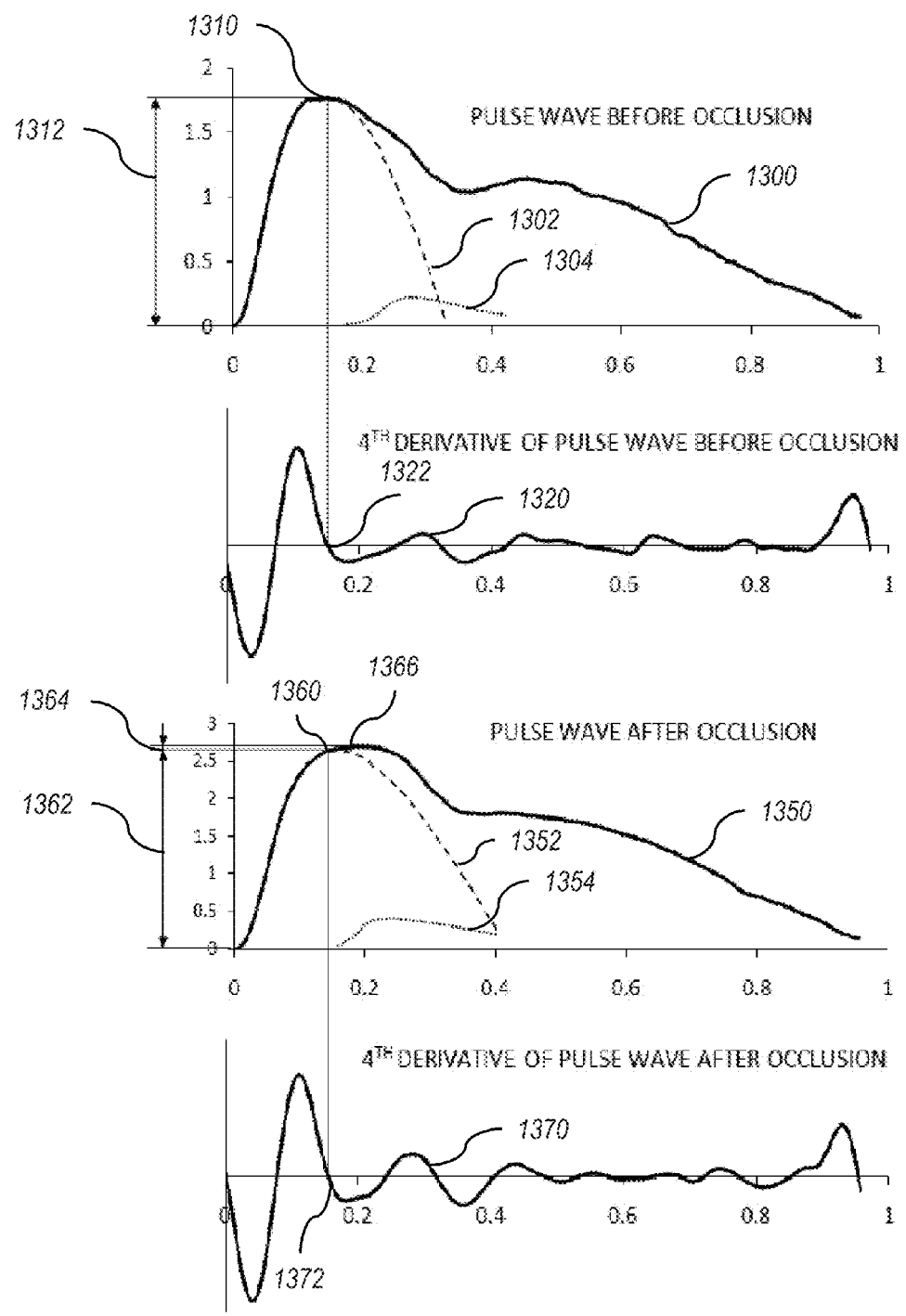
FIG. 13 is a timing diagram illustrating a measured pulse wave for a healthy person.

FIG. 13 is a timing diagram illustrating a measured pulse wave for a healthy person. A pulse wave 1300 includes an early systolic component 1302 and a late systolic component 1304. (The pulse wave 1300 may include other component pulse waves, which are not shown.) The early systolic component 1302 forms an inflection point 1310 in the pulse wave 1300. Because of the amplitude and the timing of the late systolic component 1304, the maximum of the pulse wave 1300 coincides with the peak of the early systolic component 1310. A line 1320 is a fourth derivative of the pulse wave 1300 and includes a third zero-line crossing point 1322. The crossing point 1322 is used to determine the time and amplitude 1312 of the early systolic component.

During the after-stimulus period, the shape of the arterial volume pulse wave changes to a pulse wave 1350. The pulse wave 1350 includes an early systolic component 1352 and a late systolic component 1354. (The pulse wave 1350 may include other component pulse waves, which are not shown.) The early systolic component 1352 forms an inflection point 1360 in the pulse wave 1350. During the after stimulus period, the amplitude and the timing of the late systolic component 1352 change slightly and the maximum 1366 of the pulse wave 1350 no longer coincides with the peak of the early systolic component 1360. Yet, the amplitude 1362 of the early systolic component 1352 and the amplitude (distance 1362 plus the distance 1364) of the maximum 1366 of the pulse wave 1350 differ slightly.

Figure 14:
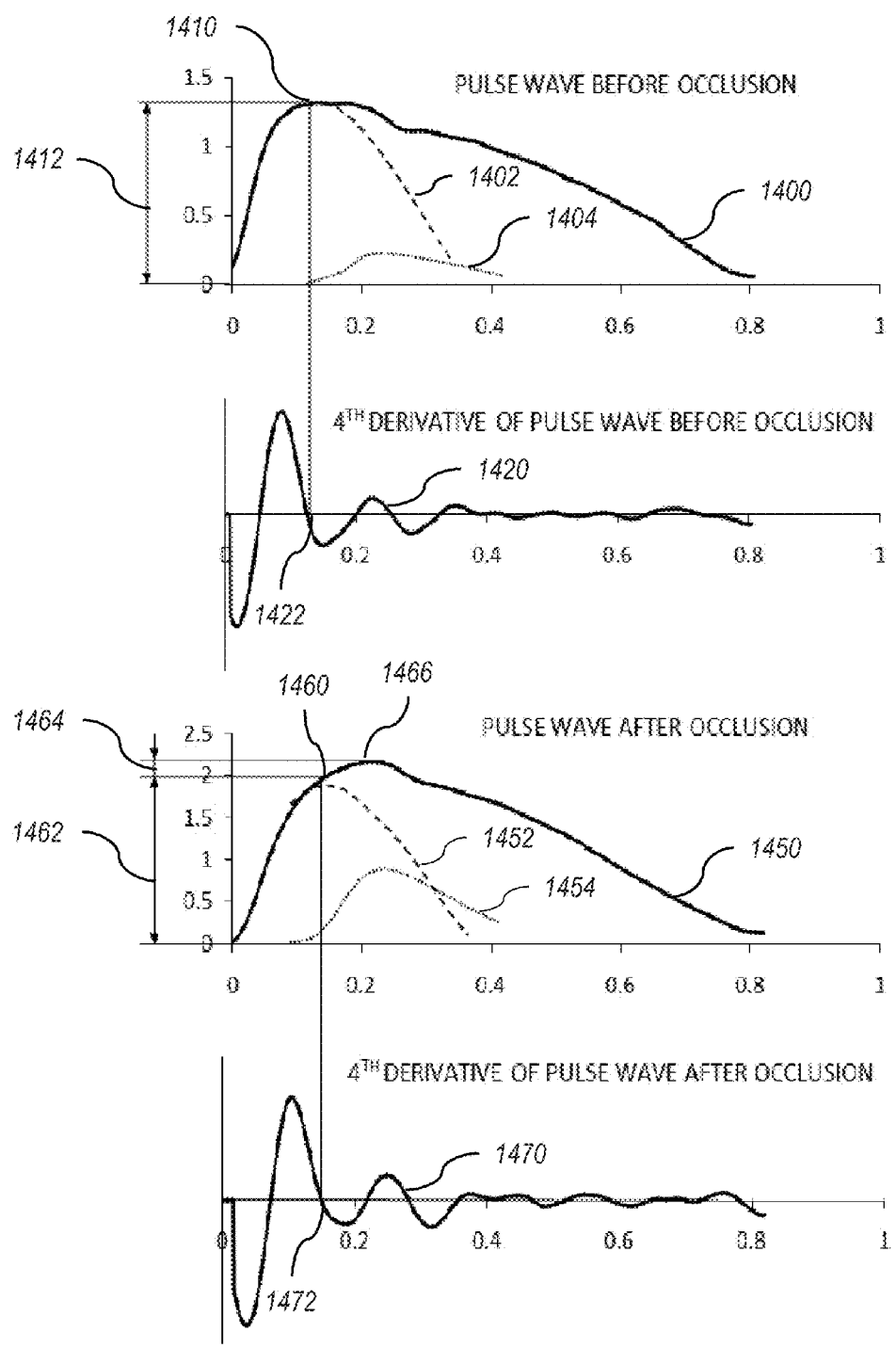
FIG. 14 is a timing diagram illustrating a measured pulse wave for a patient with cardiovascular disease.

FIG. 14 is a timing diagram illustrating a measured pulse wave for a patient with cardiovascular disease. A pulse wave 1400 includes an early systolic component 1402 and a late systolic component 1404. (The pulse wave 1400 may include other component pulse waves, which are not shown.) The early systolic component 1402 forms an inflection point 1410 in the pulse wave 1400. Because of the amplitude and the timing of the late systolic component 1404, the maximum of the pulse wave 1400 coincides with the peak of the early systolic component 1410. A line 1420 is a fourth derivative of the pulse wave 1400 and includes a third zero-line crossing point 1422. The crossing point 1422 is used to determine the time and amplitude 1412 of the early systolic component.

During the after-stimulus period, the shape of the arterial volume pulse wave changes to a pulse wave 1450. A pulse wave 1450 includes an early systolic component 1452 and a late systolic component 1454. (The pulse wave 1450 may include other component pulse waves, which are not shown.) The early systolic component 1452 forms an inflection point 1460 in the pulse wave 1450. During the after stimulus period the amplitude and the timing of the late systolic component change significantly and the maximum 1466 of the pulse wave 1450 no longer coincides with the peak of the early systolic component 1460. The amplitude 1462 of the early systolic component 1452 and the amplitude (distance 1462 plus the distance 1464) of the maximum 1466 of the pulse wave 1450 differ significantly.

The diagnostic system 100 may use the differences in the pulse wave characteristics of FIGS. 13-14 to compute arterial indexes (for instance, the augmentation index) to assess the cardiovascular status of the patient.

Figure 15:
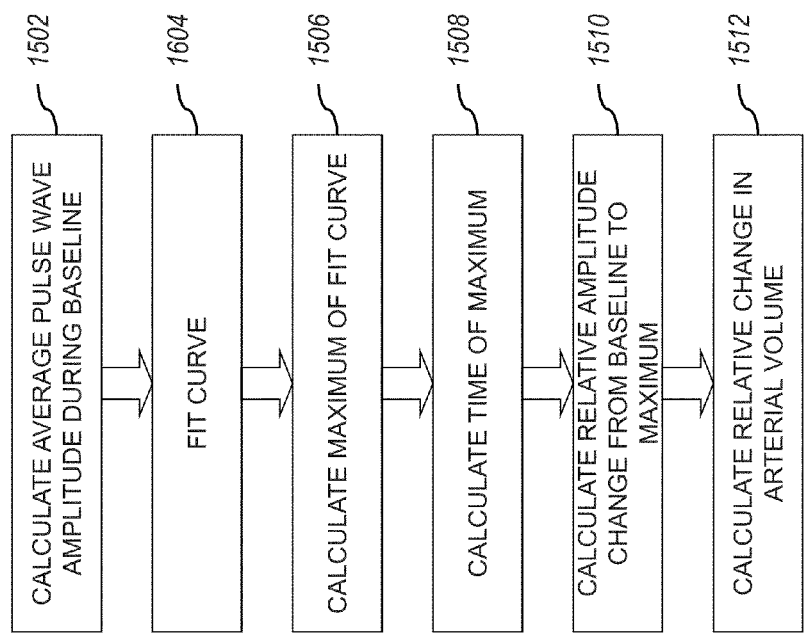
FIG. 15 is a flow chart illustrating one embodiment of an operation of determining changes in arterial volume of the operations of FIGS. 3 and 11.

FIG. 15 is a flow chart illustrating one embodiment of an operation of determining changes in arterial volume of the operations of FIGS. 3 and 11. The diagnostic computer 104 determines average pulse wave amplitude per each inflation/deflation cycle over the measurement period and obtains a graph such as the graph described above in conjunction with FIG. 5.

The diagnostic computer 104 calculates an average ($AVG_{baseline}$) of the calculated average amplitudes of the early systolic components of pulse wave measured during the baseline 402 (block 1502). For the after-stimulus period 406, the diagnostic computer 104 calculates a curve that fits the after-stimulus data of the early systolic components of pulse wave measured during the after-stimulus 406 (block 1504), using for example, a fourth-order polynomial function. The diagnostic computer 104 calculates a maximum ($MAX_{after}$) of the fitted curve of the after-stimulus data (block 1506). The diagnostic computer 104 calculates a time from the end of the occlusion (or other stimulus) to the maximum of the fitted curve of the after-stimulus data (block 1508). The diagnostic computer 104 calculates a relative amplitude change from the baseline to the maximum of the fitted curve of the after-stimulus data (block 1510).

The diagnostic computer 104 calculates relative change in arterial volume $\Delta V$ (block 1512) as follows:

$$\Delta V = [(MAX_{after} - AVG_{baseline})/AVG_{baseline}]$$

The diagnostic computer 104 calculates relative change in arterial radius as follows (block 1512):

$$\Delta R = [(\Delta V + 1)^{1/2} - 1],$$

The relative change in radius $\Delta R$ is defined as follows:

$$\Delta R = [(R_{after} - R_{baseline})/R_{baseline}],$$

where $R_{after}$ is the maximum after-stimulus radius of the artery and $R_{baseline}$ is the arterial radius at baseline.

In some embodiments, the diagnostic computer 104 may compute an area under the fitted curve for the after-stimulus data, in addition to or instead of the determination of the maximum of the fitted curve of block 1506. In some embodiments, the diagnostic computer 104 determines the area under the curve by integrating the fitted polynomial function of block 1504 from the time the stimulus ends to either the time when the measured amplitude returns to the baseline or to the end of the test. In some embodiments, the diagnostic computer 104 extrapolates the fitted curve of block 1504 to the time at which the measured amplitude returns to baseline. In some embodiments, the diagnostic computer 104 computes other parameters (e.g., the width at half-height) from the fitted curve of block 1504 to calculate the relative change in arterial volume.

The diagnostic computer 104 may provide any or all of the raw data and processed data to a doctor or clinical researcher via a display, paper or other manners well known to those skilled in the art. In some embodiments, the diagnostic computer 104 provides a doctor processed data such as 1) relative % change in arterial volume of a limb segment after a stimulus (for example, after 5 min cuff occlusion, the arterial volume changed by 57%) as a reflection of the ability of the arteries to dilate in response to the stimulus; 2) computed relative maximum % change in the radius of the artery after the stimulus; 3) time to maximum change in arterial volume (for instance, 72 sec); 4) area under the curve; and 5) pulse wave characteristics (time difference between the peaks of early and late systolic waves, augmentation index, etc.) as indicators of arterial stiffness. In some embodiments, the diagnostic computer 104 provides a doctor raw data, such as detected volume pulse waves in each inflation/deflation cycle.

Although the diagnostic system 100 is described as including one cuff 106, other numbers of cuffs 106 may be used. In some embodiments, the diagnostic system 100 includes two cuffs 106. One cuff 106 is disposed on the limb 120 and occludes the artery 122, and the other cuff 106 is disposed on the limb 120 distal to the first cuff 106, and detects the pressure oscillations. Alternatively, one cuff 106 is disposed on the limb 120 and detects the pressure in the artery 122, and the other cuff 106 is disposed on the limb 120 distal to the first cuff 106, and occludes the artery 122.

Reference in the specification to "some embodiments" means that a particular feature, structure, or characteristic described in connection with the embodiments is included in at least one embodiment of the invention. The appearances of the phrase "in some embodiments" in various places in the specification are not necessarily all referring to the same embodiment.

Some portions of the detailed description that follows are presented in terms of algorithms and symbolic representations of operations on data bits within a computer memory. These algorithmic descriptions and representations are the means used by those skilled in the data processing arts to most effectively convey the substance of their work to others skilled in the art. An algorithm is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

However, all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects of the present invention include process steps and instructions described herein in the form of an algorithm. It should be noted that the process steps and instructions of the present invention could be embodied in software, firmware or hardware, and when embodied in software, could be downloaded to reside on and be operated from different platforms used by a variety of operating systems.

The present invention also relates to an apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The algorithms and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the present invention is not described with reference to any particular programming language. It will be appreciated that a variety of programming languages may be used to implement the teachings of the present invention as described herein, and any references below to specific languages are provided for disclosure of enablement and best mode of the present invention.

While particular embodiments and applications of the present invention have been illustrated and described herein, it is to be understood that the invention is not limited to the precise construction and components disclosed herein and that various modifications, changes, and variations may be made in the arrangement, operation, and details of the methods and apparatuses of the present invention without departing from the spirit and scope of the invention as it is defined in the appended claims.

What is claimed is:

1. A method for assessing change in arterial volume of a limb segment of a mammal, said method comprising:
    determining amplitudes of component pulse waves of detected volume pulse waves of a limb segment detected during a baseline period to determine a baseline arterial volume of the limb segment;
    applying a stimulus to the mammal to induce a period of change in the arterial volume of the limb segment;
    determining amplitudes of component pulse waves of detected volume pulse waves of the limb segment detected during a time period after the stimulus has been applied to the mammal to induce a period of change in the arterial volume of the limb segment; and
    determining relative change in arterial volume of the limb segment during the time period after the stimulus relative to the arterial volume of the limb segment during the baseline period from the amplitudes of the component pulse waves of the detected volume pulse waves during the baseline and after the stimulus;
    wherein determining relative change in arterial volume of the limb comprises:
        calculating an average component pulse wave amplitude during the baseline period;
        generating a curve fit of component pulse wave amplitudes during the after-stimulus period;
        calculating a maximum of the fitted curve;
        determining a time between beginning of the after-stimulus period and the time of the maximum of the fitted curve;
        determining a relative amplitude change from the baseline to the maximum of the fitted curve; and
        determining a relative change in arterial volume from the relative amplitude change from the baseline to the maximum of the fitted curve and the average component pulse wave amplitude during the baseline period.

2. The method of claim 1, wherein the component pulse wave is an early systolic component.

3. The method of claim 2 wherein the determining relative change in arterial volume includes comparing maximum amplitudes of the early systolic components of the volume pulse waves during the baseline period and maximum amplitudes of the early systolic components of the volume pulse waves after the stimulus.

4. The method of claim 2, wherein determining amplitude of early systolic component of a volume pulse wave comprises:
    determining an occurrence of an inflection point in the volume pulse wave;
    determining a time of the occurrence of the inflection point;
    determining a pressure value on the detected volume pulse wave at said time;
    determining a pressure value at the beginning of the volume pulse wave; and
    assessing the amplitude of the early systolic component of the volume pulse wave as the difference between said pressures values.

5. The method of claim 1, further comprising:
    monitoring the limb segment to record the detected volume pulse waves of the limb segment during the baseline period;
    monitoring the limb segment to record the detected volume pulse waves of the limb segment during a period of an after-stimulus period.

6. The method of claim 5 wherein the component pulse wave is an early systolic component.

7. The method of claim 1, wherein the stimulus comprises a mechanical stimulation, a thermal stimulation, a chemical stimulation, an electrical stimulation, a neurological stimulation, a mental stimulation or a physical exercise stimulation, or any combination thereof, to induce a change in arterial volume of the limb segment.

8. The method of claim 1, wherein applying the stimulus comprises inflating a cuff that is disposed on the limb segment to a pressure above systolic for a period of time sufficient to induce change in arterial volume of the limb segment after releasing the inflation pressure of the cuff.

9. The method of claim 8, further comprising:
    monitoring blood oxygen in the limb distal to the cuff to standardize a degree of limb ischemia among a plurality of test subjects; and
    quantifying an amount of stimulus in a particular patient in response to the standardized degree of limb ischemia among the plurality of test subjects.

10. The method of claim 1 wherein calculating an average pulse wave amplitude during the baseline comprises:
    determining an average pulse wave amplitude for each inflation/deflation cycle of a plurality of inflation/deflation cycles over the baseline period; and
    calculating an average pulse wave amplitude during the baseline from the average pulse wave amplitudes of the plurality of inflation/deflation cycles.

11. The method of claim 1 wherein generating a curve fit of pulse wave amplitudes comprises generating a fourth-order polynomial function to fit the after-stimulus pulse wave amplitudes.

12. The method of claim 1, wherein determining relative change in arterial volume of the limb further comprises integrating an area under the fitted curve from a time period of the end of the stimulus to a time when the measured amplitude returns to a baseline amplitude.

13. A method for assessing change in arterial volume of a limb segment of a mammal, said method comprising:
    monitoring a limb segment to record detected volume pulse waves of the limb segment during a baseline period;
    determining amplitudes of component pulse waves of the detected volume pulse waves of the limb segment detected during the baseline period to determine a baseline arterial volume of the limb segment;
    applying a stimulus to the mammal to induce a period of change in the arterial volume of the limb segment;

monitoring the limb segment to record detected volume pulse waves of the limb segment during an after-stimulus period after the stimulus has been applied;

determining amplitudes of component pulse waves of detected volume pulse waves of the limb segment detected during the after-stimulus period; and determining relative change in arterial volume of the limb segment during the after-stimulus period relative to the arterial volume of the limb segment during the baseline period from the amplitudes of the component pulse waves of the detected volume pulse waves during the baseline and after-stimulus periods;

wherein monitoring the limb segment during the baseline and after-stimulus periods each comprise:

applying, in a series, an external pressure to the limb segment at a mean arterial pressure of the limb; and detecting volume pulse waves of the limb segment.

14. A method for assessing change in arterial volume of a limb segment of a mammal, said method comprising:

monitoring a limb segment to record detected volume pulse waves of the limb segment during a baseline period;

determining amplitudes of component pulse waves of the detected volume pulse waves of the limb segment detected during the baseline period to determine a baseline arterial volume of the limb segment;

applying a stimulus to the mammal to induce a period of change in the arterial volume of the limb segment;

monitoring the limb segment to record detected volume pulse waves of the limb segment during an after-stimulus period after the stimulus has been applied;

determining amplitudes of component pulse waves of detected volume pulse waves of the limb segment detected during the after-stimulus period; and determining relative change in arterial volume of the limb segment during the after-stimulus period relative to the arterial volume of the limb segment during the baseline period from the amplitudes of the component pulse waves of the detected volume pulse waves during the baseline and after-stimulus periods;

wherein monitoring the limb segment during the baseline and after-stimulus periods each comprise:

applying an external pressure to the limb segment at a pressure level which allows blood flow through the artery to produce said volume pulse waves in response to the applied external pressure.

15. The method of claim 14, wherein applying the external pressure comprises varying gradually the external pressure between near-systolic and near-diastolic, and detecting the volume pulse waves while the external pressure is between systolic and diastolic.

16. The method of claim 14, wherein applying the external pressure comprises:

initially applying the external pressure at a pressure near systolic, and gradually reducing the external pressure to a pressure near diastolic.

17. The method of claim 14, wherein applying the external pressure comprises:

initially applying the external pressure at a pressure near diastolic, and gradually increasing to a pressure near systolic.

18. The method of claim 14, wherein applying the external pressure comprises cycling the external pressure between a high level and a low level, wherein determining the amplitudes of component pulse waves of the volume pulse waves includes said determining while the external pressure is at the high level.

19. The method of claim 18, wherein the high level is near mean arterial pressure and the low level is below venous pressure.

20. The method of claim 18, wherein the high level is below diastolic pressure and the low level is below venous pressure.

21. A method for assessing change in arterial volume of a limb segment of a mammal, said method comprising:

determining amplitudes of component pulse waves of detected volume pulse waves of a limb segment detected during a baseline period to determine a baseline arterial volume of the limb segment;

applying a stimulus to the mammal to induce a period of change in the arterial volume of the limb segment;

determining amplitudes of component pulse waves of detected volume pulse waves of the limb segment detected during a time period after a stimulus has been and determining relative change in arterial volume of the limb segment during the time period after the stimulus relative to the arterial volume of the limb segment during the baseline period from the amplitudes of the component pulse waves of the detected volume pulse waves during the baseline and after the stimulus;

wherein the component pulse wave is an early systolic component; and wherein determining amplitude of early systolic component of a volume pulse wave comprises:

computing a fourth derivative of the detected volume pulse wave;

determining a time at which the fourth derivative reaches a third zero crossing;

determining a pressure value on the detected volume pulse wave at said time;

determining a pressure value at the beginning of the volume pulse wave; and assessing the amplitude of the early systolic component of the volume pulse wave as the difference between said pressures values.

22. The method of claim 21 wherein the determining the pressure value at the beginning of the volume pulse wave includes determining a minimum of the pulse wave corresponding to a diastole of a heart.

23. A diagnostic system for assessing change in arterial volume of a limb segment of a mammal comprising:

a sensor for detecting volume pulse waves of a limb segment during a baseline period and for detecting volume pulse waves of the limb segment during a period of an after-stimulus change in arterial volume;

a processor coupled to the sensor to determine amplitudes of component pulse waves of detected volume pulse waves of the limb segment detected during the baseline period to determine a baseline arterial volume of the limb segment, to determine amplitudes of component pulse waves of detected volume pulse waves of the limb segment detected during a time period after a stimulus has been applied to the mammal to induce a period of change in the arterial volume of the limb segment, and to determine relative change in arterial volume of the limb segment during the time period after the stimulus relative to the arterial volume of the limb during the baseline period from the amplitudes of the component pulse waves of the detected volume pulse waves at baseline and after the stimulus;

wherein the processor calculates an average pulse wave amplitude during the baseline period, generates a curve fit of pulse wave amplitudes during the after-stimulus period, calculates a maximum of the fitted curve, determines a time between beginning of the after-stimulus period and the time of the maximum of the fitted curve, determines a relative amplitude change from the baseline to the maximum of the fitted curve, and determines a relative change in arterial volume from the relative amplitude change from the baseline to the maximum of the fitted curve and the average pulse wave amplitude during the baseline period to determine relative change in arterial volume of the limb.

24. The diagnostic system of claim 23, wherein the processor determines the relative change in arterial volume by comparing the amplitudes of the component pulse waves of volume pulse waves at baseline and after the stimulus.

25. The diagnostic system of claim 23, wherein the component pulse wave is an early systolic component.

26. The diagnostic system of claim 25, wherein the processor determines the relative change in arterial volume by comparing maximum amplitudes of the early systolic components of the volume pulse waves during the baseline period and maximum amplitudes of the early systolic components of the volume pulse waves after the stimulus.

27. The diagnostic system of claim 25, wherein the processor determines an occurrence of an inflection point in the volume pulse wave, determines a time of the occurrence of the inflection point, determines a pressure value on the detected volume pulse wave at said time, determines a pressure value at the beginning of the volume pulse wave, and assesses the amplitude of the early systolic component of the volume pulse wave as the difference between said pressures values to determine the amplitude of early systolic component of a volume pulse wave.

28. The diagnostic system of claim 23, further comprising a pressure cuff coupled to the sensor and the processor for applying a pressure to the limb segment to occlude an artery in the limb segment and for releasing said pressure to the limb segment to allow blood flow in the artery to induce the period of change in arterial volume of the limb segment in response to a control signal from the processor.

29. The diagnostic system of claim 23, further comprising a pressure cuff coupled to the sensor and the processor to apply a stimulus to the mammal to induce a period of change in arterial volume of the limb segment.

30. The diagnostic system of claim 23, further comprising a pressure cuff coupled to the sensor and the processor to apply a stimulus to the mammal by inflating to a pressure above systolic for application to the limb segment for a period of time sufficient to induce change in arterial volume of the limb segment after releasing the inflation pressure of the cuff.

31. The diagnostic system of claim 30, further comprising:
a blood oxygen sensor coupled to the processor to monitor the limb distal to the cuff to standardize a degree of limb ischemia among a plurality of test subjects; and
wherein the processor quantifies an amount of stimulus in a particular patient in response to the standardized degree of limb ischemia among the plurality of test subjects.

32. The diagnostic system of claim 23, wherein the processor determines an average pulse wave amplitude for each inflation/deflation cycle of a plurality of inflation/deflation cycles over the baseline period, and calculates an average pulse wave amplitude during the baseline from the average pulse wave amplitudes of the plurality of inflation/deflation cycles to calculate an average pulse wave amplitude during the baseline.

33. The diagnostic system of claim 23, wherein the processor generates a fourth-order polynomial function to fit the after-stimulus pulse wave amplitudes to generate a curve fit of pulse wave amplitudes.

34. The diagnostic system of claim 23, wherein the processor integrates an area under the fitted curve from a time period of the end of the stimulus to a time when the measured amplitude returns to a baseline amplitude to determine relative change in arterial volume of the limb.

35. A diagnostic system for assessing change in arterial volume of a limb segment of a mammal comprising:
a sensor for detecting volume pulse waves of a limb segment during a baseline period and for detecting volume pulse waves of the limb segment during a period of an after-stimulus change in arterial volume;
a processor coupled to the sensor to determine amplitudes of component pulse waves of detected volume pulse waves of the limb segment detected during the baseline period to determine a baseline arterial volume of the limb segment, to determine amplitudes of component pulse waves of detected volume pulse waves of the limb segment detected during a time period after a stimulus has been applied to the mammal to induce a period of change in the arterial volume of the limb segment, and to determine relative change in arterial volume of the limb segment during the time period after the stimulus relative to the arterial volume of the limb during the baseline period from the amplitudes of the component pulse waves of the detected volume pulse waves at baseline and after the stimulus; and
a pressure cuff coupled to the sensor and the processor to apply a stimulus to the mammal by inflating to a pressure above systolic for application to the limb segment for a period of time sufficient to induce change in arterial volume of the limb segment after releasing the inflation pressure of the cuff;
wherein the processor controls the cuff to apply, in a series, an external pressure to the limb segment at a mean arterial pressure of the limb, and controls the sensor to detect volume pulse waves of the limb segment during the baseline and after the stimulus.

36. A diagnostic system for assessing change in arterial volume of a limb segment of a mammal comprising:
a sensor for detecting volume pulse waves of a limb segment during a baseline period and for detecting volume pulse waves of the limb segment during a period of an after-stimulus change in arterial volume;
a processor coupled to the sensor to determine amplitudes of component pulse waves of detected volume pulse waves of the limb segment detected during the baseline period to determine a baseline arterial volume of the limb segment, to determine amplitudes of component pulse waves of detected volume pulse waves of the limb segment detected during a time period after a stimulus has been applied to the mammal to induce a period of change in the arterial volume of the limb segment, and to determine relative change in arterial volume of the limb segment during the time period after the stimulus relative to the arterial volume of the limb during the baseline period from the amplitudes of the component pulse waves of the detected volume pulse waves at baseline and after the stimulus; and
a pressure cuff coupled to the sensor and the processor to apply a stimulus to the mammal by inflating to a pressure above systolic for application to the limb segment for a period of time sufficient to induce change in arterial volume of the limb segment after releasing the inflation pressure of the cuff;

wherein the processor controls the cuff to apply an external pressure to the limb segment at a pressure level which allows blood flow through the artery to produce said volume pulse waves in response to the applied external pressure during the baseline and after the stimulus.

37. The diagnostic system of claim 36, wherein the processor controls the cuff to apply the external pressure to the limb segment as a gradually varying pressure between near-systolic and near-diastolic, and wherein the processor controls the sensor to detect the volume pulse waves while the external pressure is between systolic and diastolic.

38. The diagnostic system of claim 36, wherein the processor controls the cuff to apply the external pressure to the limb segment at a pressure near systolic, and gradually reducing the pressure to near diastolic.

39. The diagnostic system of claim 36, wherein the processor controls the cuff to apply the external pressure to the limb segment at a pressure near diastolic, and gradually increasing to the pressure to near systolic.

40. The diagnostic system of claim 36, wherein the processor controls the cuff to cycle the external pressure applied to the limb segment between a high level and a low level, wherein the processor determines the amplitudes of component pulse waves of the volume pulse waves detected while the external pressure is at the high level.

41. The diagnostic system of claim 36, wherein the high level is near mean arterial pressure and the low level is below venous pressure.

42. The diagnostic system of claim 36, wherein the high level is below diastolic pressure and the low level is below venous pressure.

43. A diagnostic system for assessing change in arterial volume of a limb segment of a mammal comprising:

a sensor for detecting volume pulse waves of a limb segment during a baseline period and for detecting volume pulse waves of the limb segment during a period of an after-stimulus change in arterial volume; and a processor coupled to the sensor to determine amplitudes of component pulse waves of detected volume pulse waves of the limb segment detected during the baseline period to determine a baseline arterial volume of the limb segment, to determine amplitudes of component pulse waves of detected volume pulse waves of the limb segment detected during a time period after a stimulus has been applied to the mammal to induce a period of change in the arterial volume of the limb segment, and to determine relative change in arterial volume of the limb segment during the time period after the stimulus relative to the arterial volume of the limb during the baseline period from the amplitudes of the component pulse waves of the detected volume pulse waves at baseline and after the stimulus;

wherein the component pulse wave is an early systolic component; and wherein the processor computes a fourth derivative of the detected volume pulse wave, determines a time at which the fourth derivative reaches a third zero crossing, determines a pressure value on the detected volume pulse wave at said time, determines a pressure value at the beginning of the volume pulse wave, and assesses the amplitude of the early systolic component of the volume pulse wave as the difference between said pressures values to determine the amplitude of early systolic component of a volume pulse wave.

44. The diagnostic system of claim 43, wherein the processor determines a minimum of the pulse wave corresponding to a diastole of a heart of the mammal to determine the pressure value at the beginning of the volume pulse wave.

45. A non-transitory machine-readable medium encoded with instructions, that when executed by one or more processors, cause the processor to carry out a process for assessing change in arterial volume of a limb segment of a mammal, the process comprising:

determining amplitudes of component pulse waves of detected volume pulse waves of a limb segment detected during a baseline period to determine a baseline arterial volume of the limb segment;

determining amplitudes of component pulse waves of detected volume pulse waves of the limb segment detected during a time period after a stimulus has been applied to the mammal to induce a period of change in the arterial volume of the limb segment; and determining relative change in arterial volume of the limb segment during the time period after the stimulus relative to the arterial volume of the limb during the baseline period from the amplitudes of the component pulse waves of the detected volume pulse waves at baseline and after the stimulus;

wherein determining relative change in arterial volume of the limb comprises:

calculating an average component pulse wave amplitude during the baseline period;

generating a curve fit of component pulse wave amplitudes during the after-stimulus period;

calculating a maximum of the fitted curve;

determining a time between beginning of the after-stimulus period and the time of the maximum of the fitted curve;

determining a relative amplitude change from the baseline to the maximum of the fitted curve; and determining a relative change in arterial volume from the relative amplitude change from the baseline to the maximum of the fitted curve and the average component pulse wave amplitude during the baseline period.

46. The non-transitory machine-readable medium encoded with instructions of claim 45, wherein the component pulse wave is an early systolic component.

47. The non-transitory machine-readable medium encoded with instructions of claim 45, wherein the instructions for determining relative change in arterial volume includes instructions for comparing maximum amplitudes of the early systolic components of the volume pulse waves during the baseline period and maximum amplitudes of the early systolic components of the volume pulse waves after the stimulus.

48. The non-transitory machine-readable medium encoded with instructions of claim 45, further comprising instructions for monitoring the limb segment to record the detected volume pulse waves of the limb segment during the baseline period, and instructions for monitoring the limb segment to record the detected volume pulse waves of the limb segment during the after-stimulus period.

49. The non-transitory machine-readable medium encoded with instructions of claim 48, wherein the component pulse wave is an early systolic component.

* * * * *